(12) United States Patent
Tanaka et al.

(10) Patent No.: US 8,273,051 B2
(45) Date of Patent: Sep. 25, 2012

(54) SELF-SEALING DEVICE AND METHOD FOR DELIVERY OF A THERAPEUTIC AGENT THROUGH A PNEUMOSTOMA

(75) Inventors: Don Tanaka, Saratoga, CA (US);
Joshua P. Wiesman, Boston, MA (US);
David C. Plough, Portola Valley, CA (US)

(73) Assignee: Portaero, Inc., Cupertino, CA (US)

( * ) Notice: Subject to any disclaimer, the term of this patent is extended or adjusted under 35 U.S.C. 154(b) by 0 days.

(21) Appl. No.: 13/213,279

(22) Filed: Aug. 19, 2011

(65) Prior Publication Data

US 2011/0306935 A1    Dec. 15, 2011

Related U.S. Application Data

(63) Continuation of application No. 12/388,470, filed on Feb. 18, 2009, now Pat. No. 8,021,320.

(60) Provisional application No. 61/029,830, filed on Feb. 19, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009, provisional application No. 61/151,581, filed on Feb. 11, 2009, provisional application No. 61/032,877, filed on Feb. 29, 2008.

(51) Int. Cl.
*A61M 1/00* (2006.01)
*A61M 37/00* (2006.01)
*A61M 25/00* (2006.01)
*A61M 31/00* (2006.01)

(52) U.S. Cl. ............. 604/27; 604/47; 604/264; 604/275

(58) Field of Classification Search .................... 604/27, 604/47, 264, 910, 93.01, 506–507, 68–72
See application file for complete search history.

(56) References Cited

U.S. PATENT DOCUMENTS

| | | | | |
|---|---|---|---|---|
| 5,178,138 A | * | 1/1993 | Walstrom et al. | 128/200.23 |
| 5,357,946 A | * | 10/1994 | Kee et al. | 128/200.24 |
| 5,807,341 A | * | 9/1998 | Heim | 604/174 |
| 6,106,495 A | * | 8/2000 | Scott | 604/93.01 |
| 7,448,385 B2 | * | 11/2008 | Wassenaar et al. | 128/206.11 |
| 2006/0130832 A1 | * | 6/2006 | Schechter et al. | 128/203.12 |
| 2006/0239930 A1 | * | 10/2006 | Lamche et al. | 424/45 |
| 2007/0163583 A1 | * | 7/2007 | Brand et al. | 128/203.23 |

* cited by examiner

*Primary Examiner* — Christopher D Koharski
*Assistant Examiner* — Rebecca E Eisenberg
(74) *Attorney, Agent, or Firm* — Fliesler Meyer LLP

(57) ABSTRACT

A pneumostoma management system includes a pneumostoma management device for maintaining the patency of a pneumostoma and a drug delivery device for pneumostoma care. The drug delivery device may be used to introduce therapeutic agents into the pneumostoma for direct treatment of the pneumostoma, treatment of the lung by way of collateral ventilation, and/or treatment of non-lung tissues by diffusion into the bloodstream. The drug delivery device includes a therapeutic agent dispenser for supplying a therapeutic agent and a propellant at positive pressure, an outlet and a connector for correctly positioning the outlet relative to a pneumostoma management device. The drug delivery device includes a self-centering and self-sealing connector for engaging the pneumostoma management device.

25 Claims, 17 Drawing Sheets

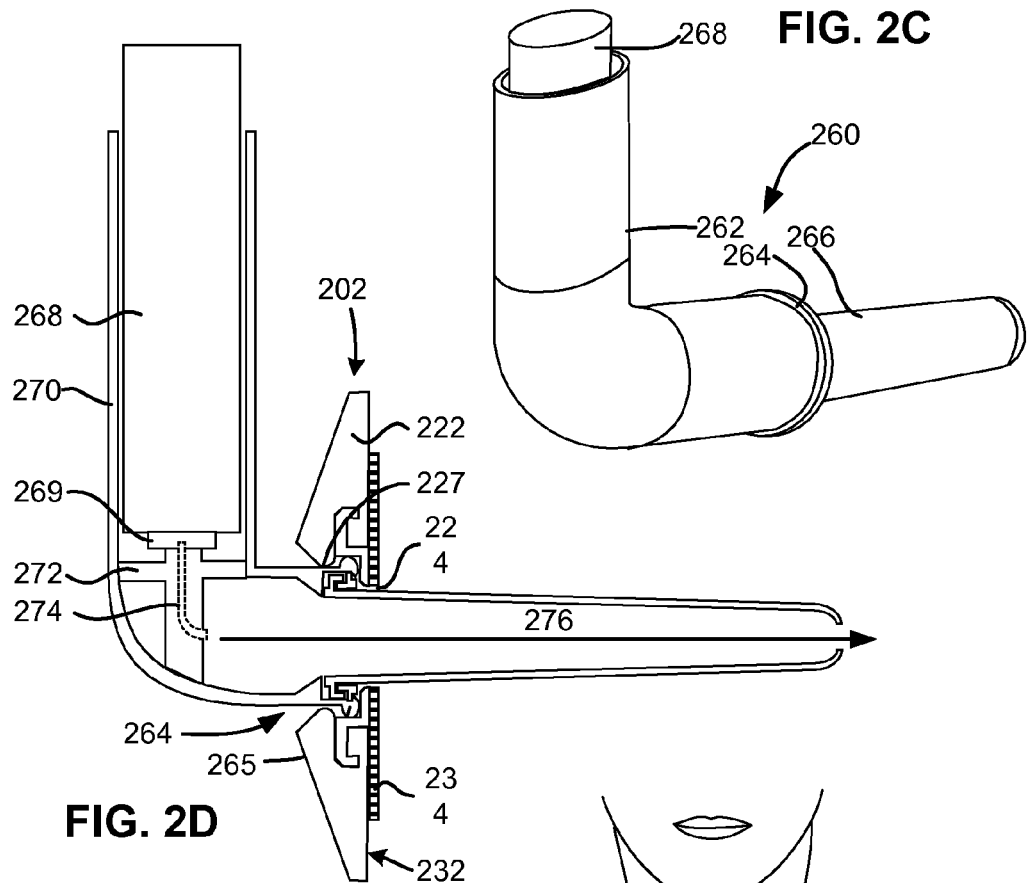
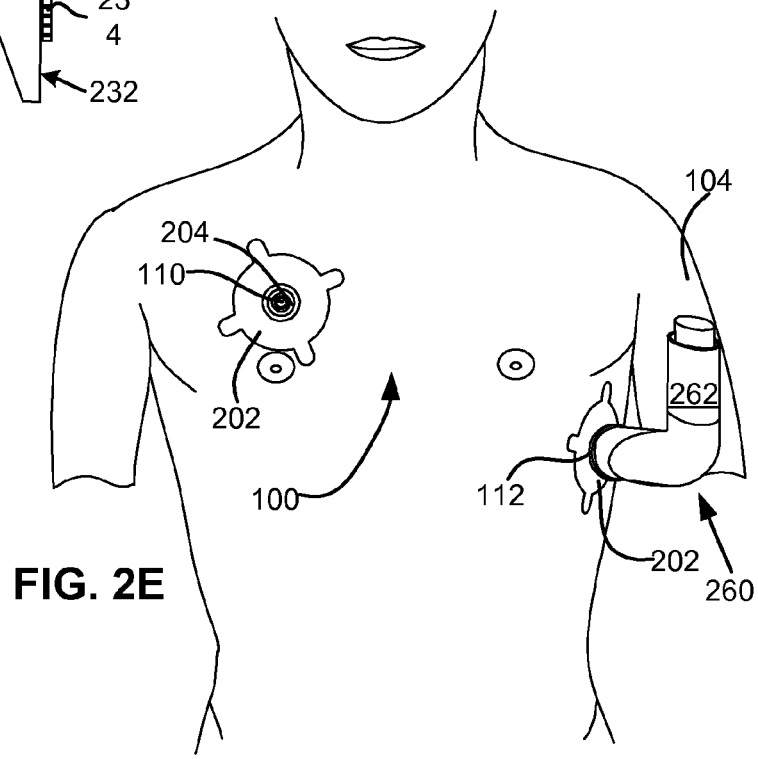
FIG. 2C
FIG. 2D
FIG. 2E

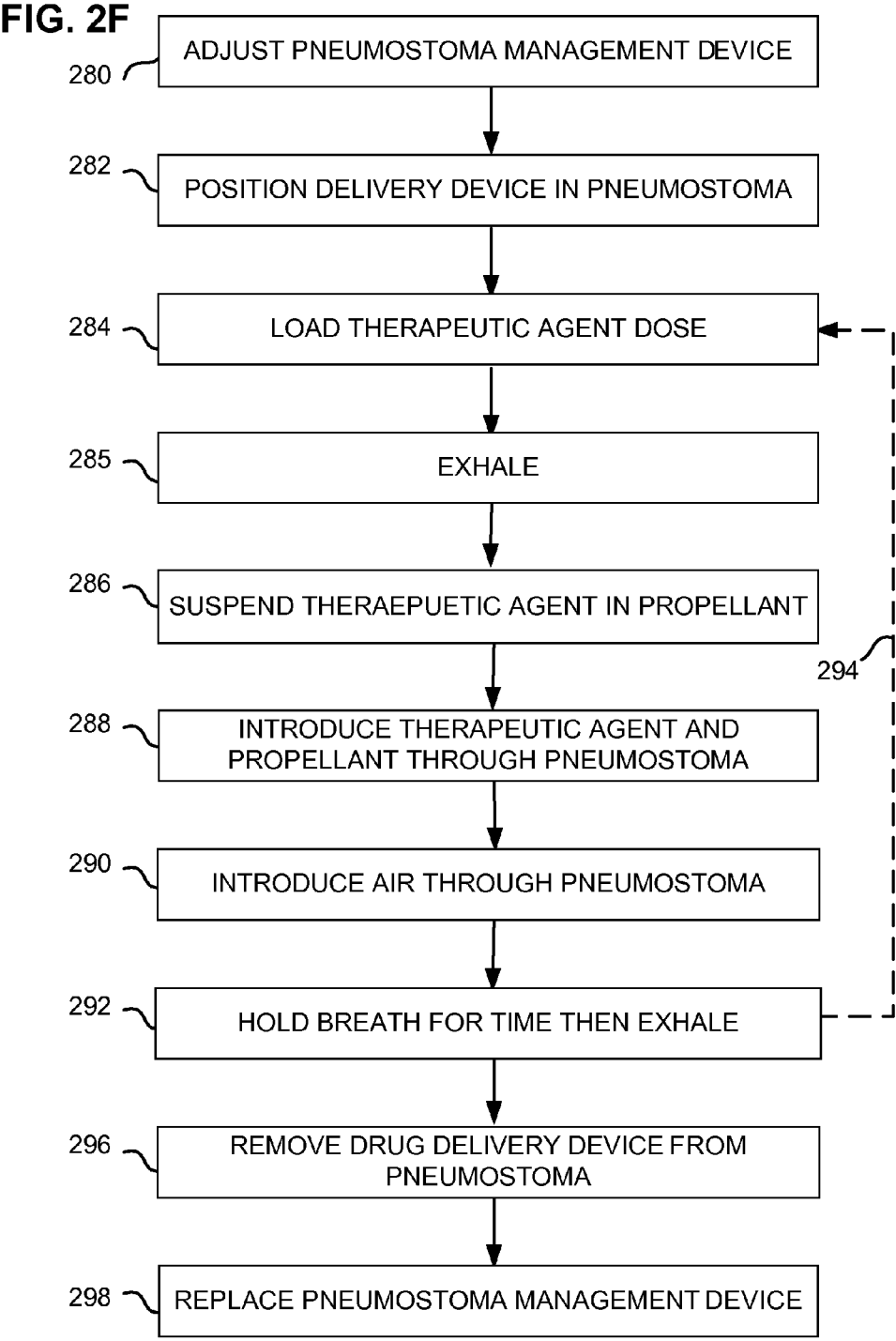

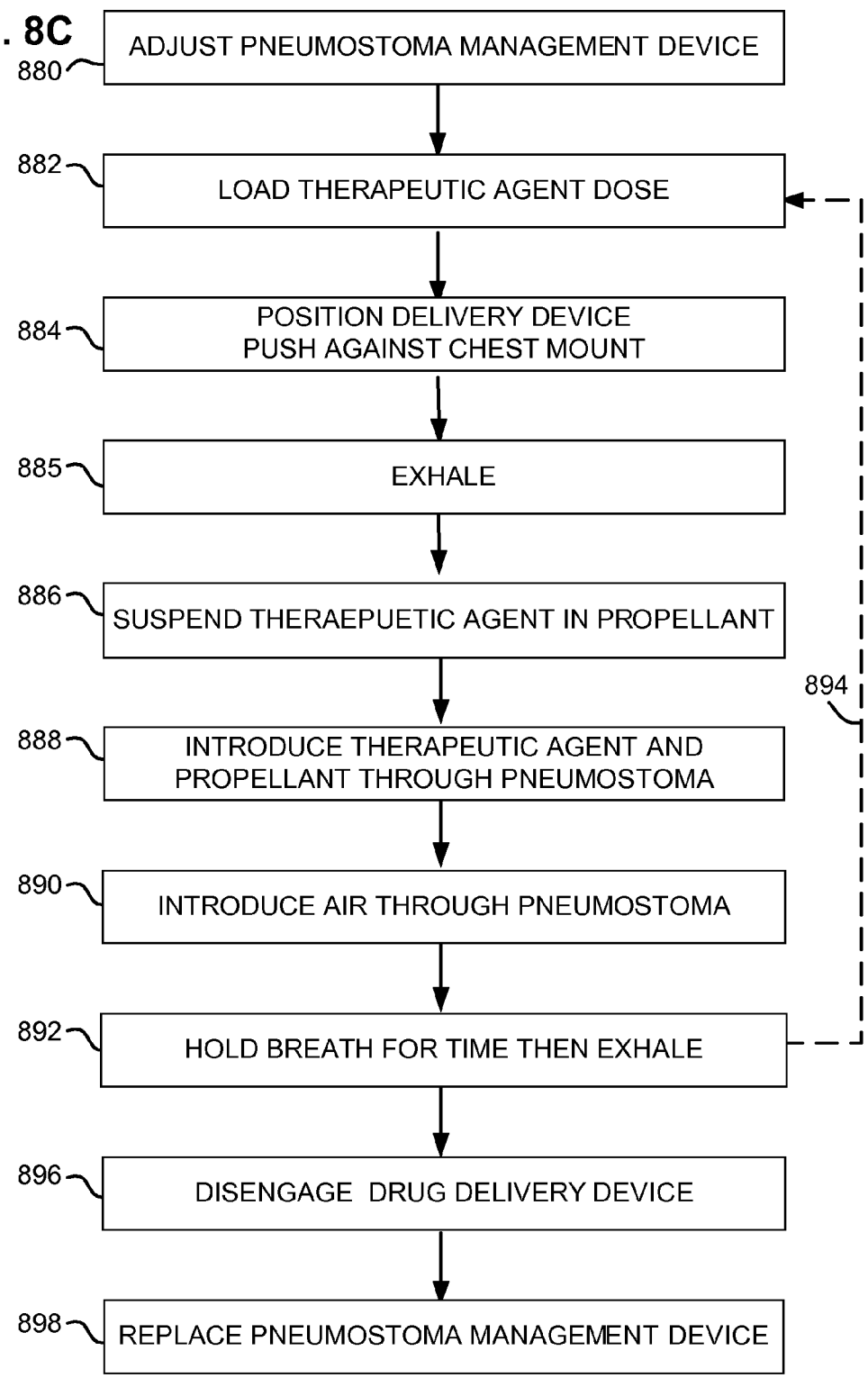

FIG. 10A
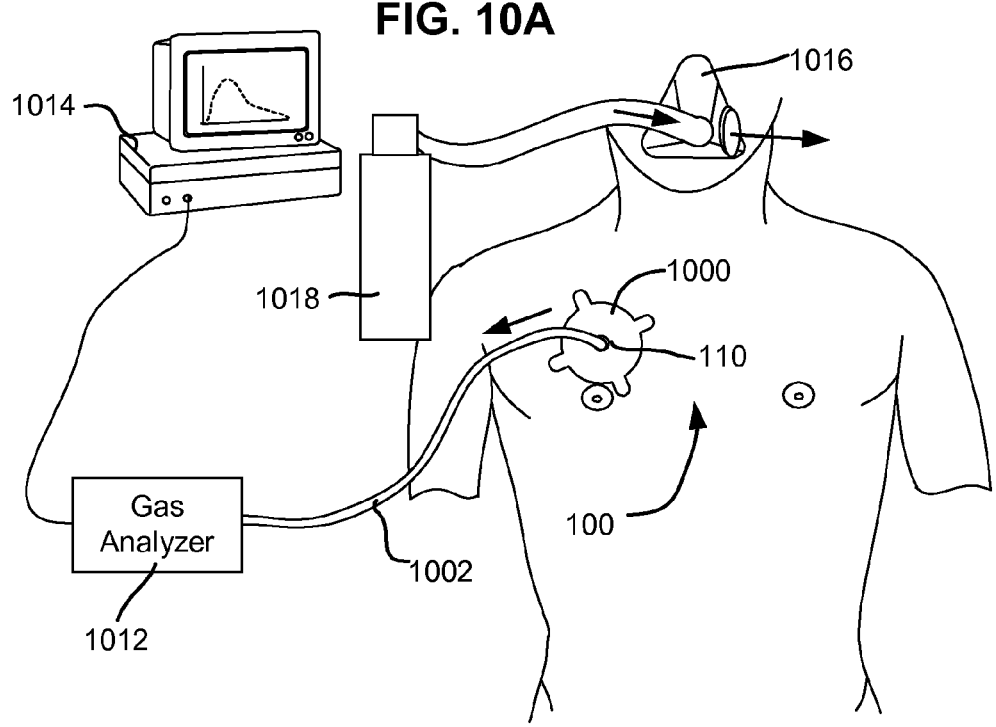
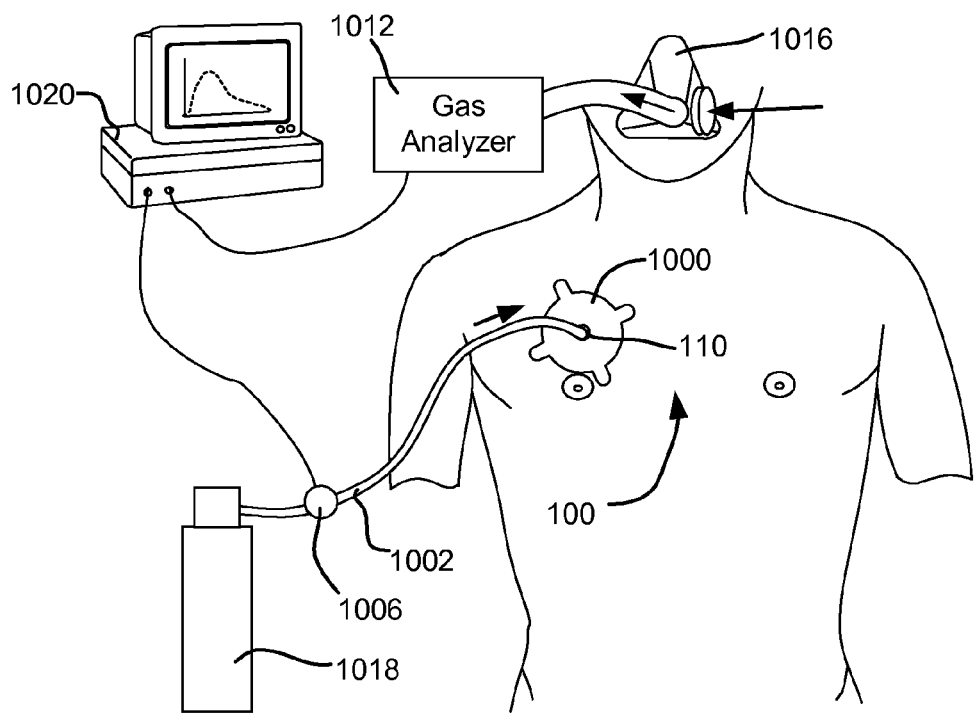
FIG. 10B

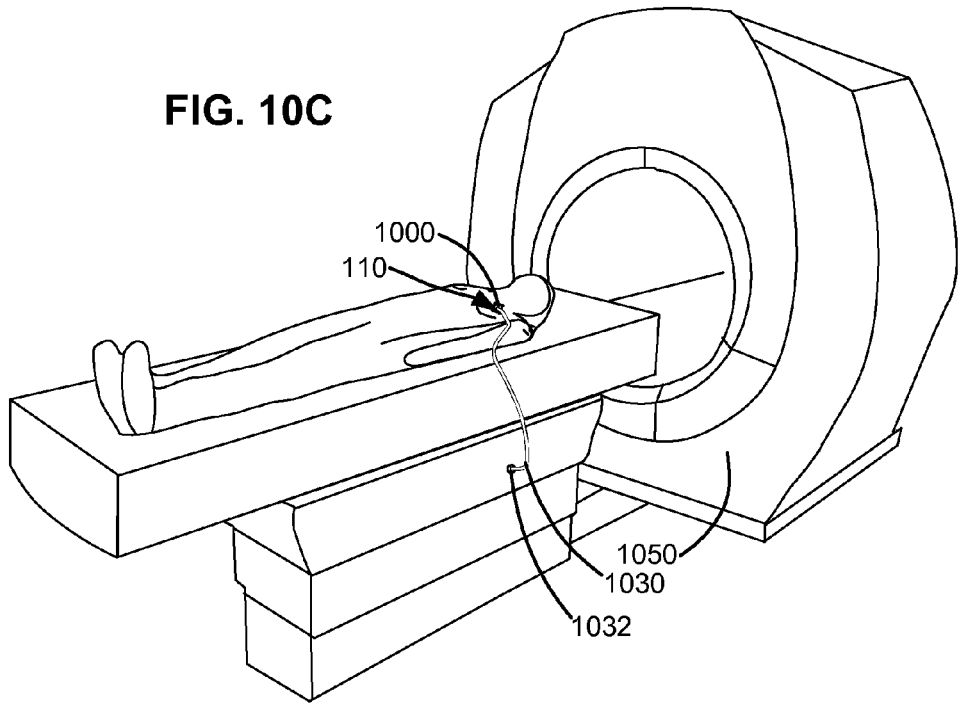
FIG. 10C
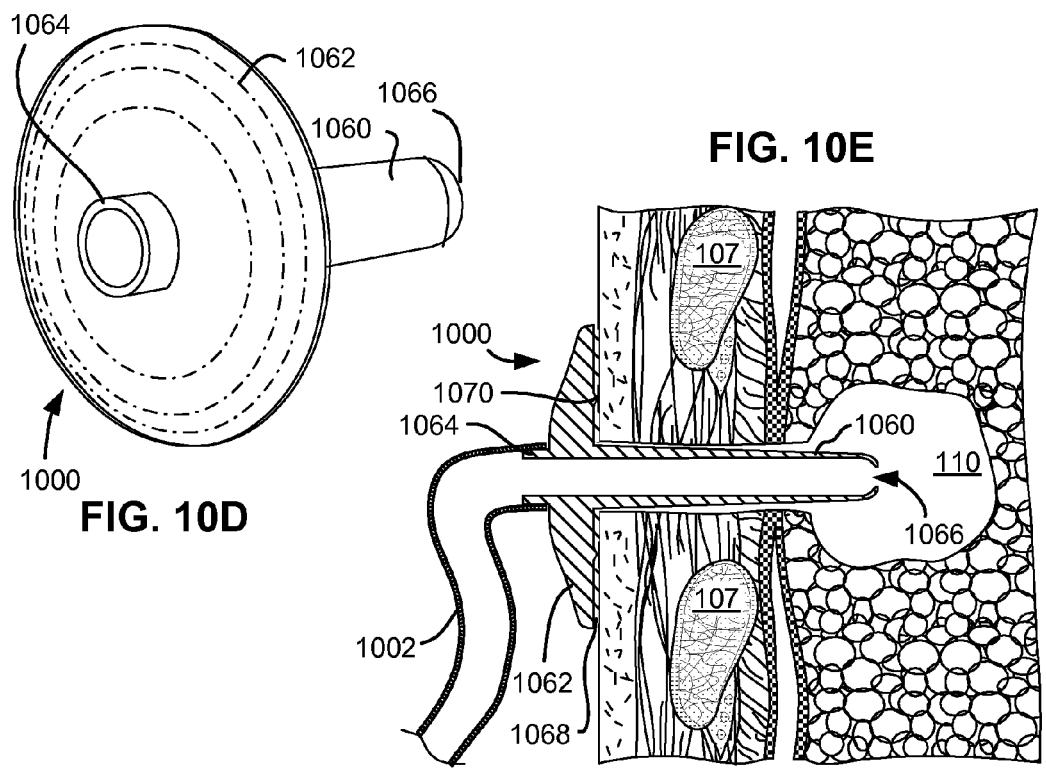
FIG. 10D
FIG. 10E

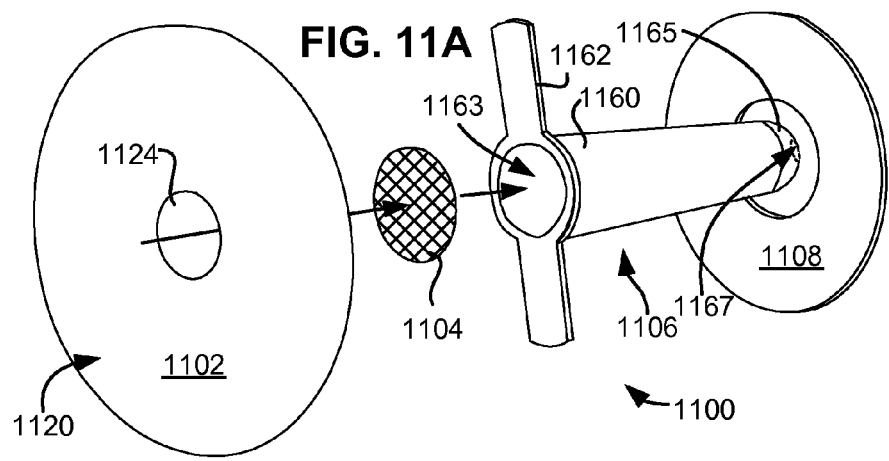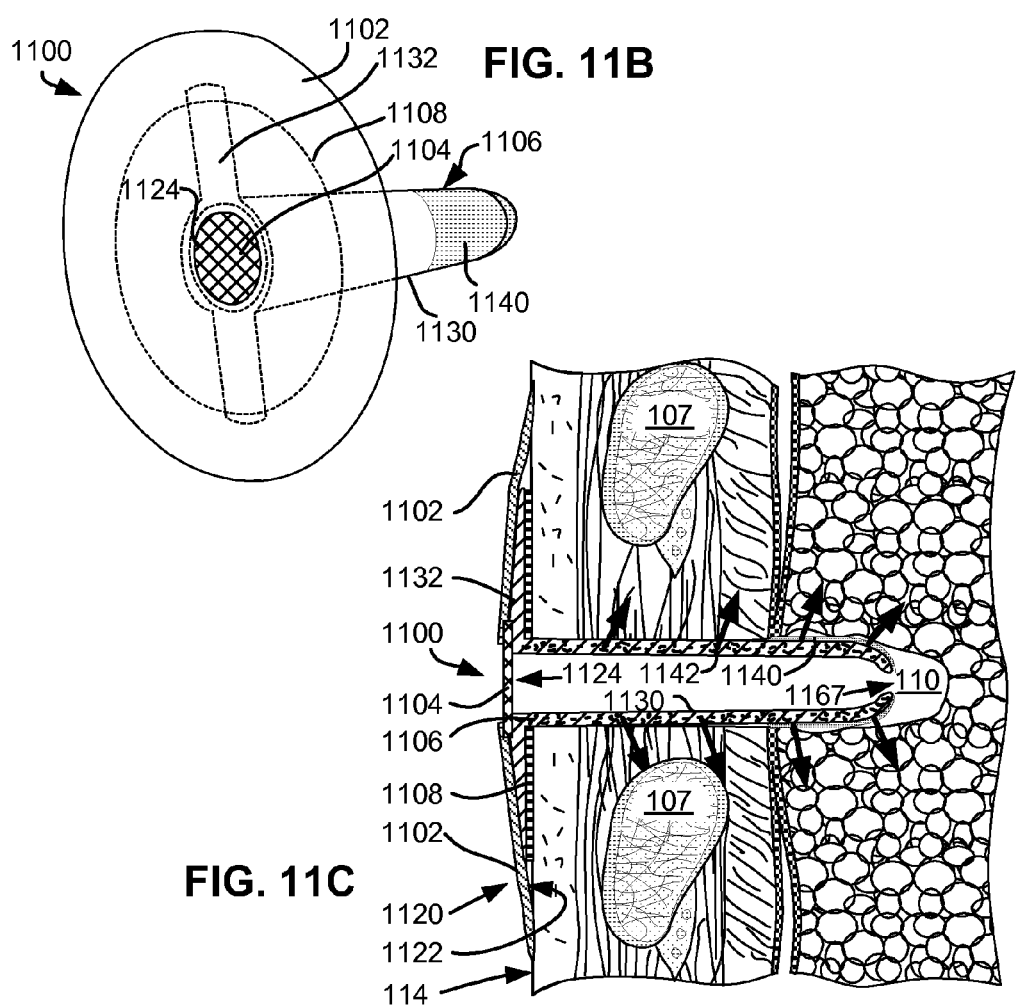

SELF-SEALING DEVICE AND METHOD FOR DELIVERY OF A THERAPEUTIC AGENT THROUGH A PNEUMOSTOMA

CLAIM TO PRIORITY

This application is a continuation of U.S. patent application Ser. No. 12/388,470, filed Feb. 18, 2009, entitled "SELF-SEALING DEVICE AND METHOD FOR DELIVERY OF A THERAPEUTIC AGENT THROUGH A PNEUMOSTOMA"; and U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE"

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE"

U.S. Provisional Application No. 61/038,371, filed Mar. 20, 2008, entitled "SURGICAL PROCEDURE AND INSTRUMENT TO CREATE A PNEUMOSTOMA AND TREAT CHRONIC OBSTRUCTIVE PULMONARY DISEASE"

U.S. Provisional Application No. 61/082,892, filed Jul. 23, 2008, entitled "PNEUMOSTOMA MANAGEMENT SYSTEM HAVING A COSMETIC AND/OR PROTECTIVE COVER"

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA"

U.S. Provisional Application No. 61/084,559, filed Jul. 29, 2008, entitled "ASPIRATOR FOR PNEUMOSTOMA MANAGEMENT"

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE"

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY" and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including U.S. patent application Ser. No. 12/388,465, filed Feb. 18, 2009, now U.S. Pat. No. 7,909,803, issued Mar. 22, 2011, entitled "ENHANCED PNEUMOSTOMA MANAGEMENT DEVICE AND METHODS FOR TREATMENT OF CHRONIC OBSTRUCTIVE PULMONARY DISEASE"

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE"

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE"

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE"

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE"

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE"

U.S. patent application Ser. No. 12/388,446, filed Feb. 18, 2009, entitled "PERCUTANEOUS SINGLE-PHASE SURGICAL PROCEDURE FOR CREATING A PNEUMOSTOMA TO TREAT CHRONIC OBSTRUCTIVE PULMONARY DISEASE"

U.S. patent application Ser. No. 12/388,460, filed Feb. 13, 2009, entitled "PNEUMOSTOMA MANAGEMENT SYSTEM HAVING A COSMETIC AND/OR PROTECTIVE COVER"

U.S. patent application Ser. No. 12/388,461, filed Feb. 18, 2009, entitled "ASPIRATOR FOR PNEUMOSTOMA MANAGEMENT"

U.S. patent application Ser. No. 12/388,462, filed Feb. 18, 2009, now U.S. Pat. No. 7,927,324, issued Apr. 29, 2011, entitled "ASPIRATOR AND METHOD FOR PNEUMOSTOMA MANAGEMENT"

U.S. patent application Ser. No. 12/388,435, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE"

U.S. patent application Ser. No. 12/388,459, filed Feb. 18, 2009, entitled "METHODS AND DEVICES FOR FOLLOW-UP CARE AND TREATMENT OF A PNEUMOSTOMA"

U.S. patent application Ser. No. 12/388,453, filed Feb. 18, 2009, entitled "SURGICAL INSTRUMENTS FOR CREATING A PNEUMOSTOMA AND TREATING CHRONIC OBSTRUCTIVE PULMONARY DISEASE"

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE"

U.S. patent application Ser. No. 12/388,467, filed Feb. 18, 2009, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE"

U.S. patent application Ser. No. 12/388,468, filed Feb. 18, 2009, entitled "MULTI-LAYER PNEUMOSTOMA MANAGEMENT SYSTEM AND METHODS FOR TREATMENT OF CHRONIC OBSTRUCTIVE PULMONARY DISEASE" and U.S. patent application Ser. No. 12/388,469, filed Feb. 18, 2009, entitled "VARIABLE LENGTH PNEUMOSTOMA MANAGEMENT SYSTEM FOR TREATMENT OF CHRONIC OBSTRUCTIVE PULMONARY DISEASE".

All of the afore-mentioned applications are incorporated herein by reference in their entireties. This patent application also incorporates by reference in their entireties all patents, applications, and articles discussed and/or cited herein.

BACKGROUND OF THE INVENTION

In the United States alone, approximately 14 million people suffer from some form of Chronic Obstructive Pulmonary Disease (COPD). However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments for ameliorating the symptoms. The goal of current treatments is to help people live with the disease more comfortably and to prevent the progression of the disease. The current options include: self-care (e.g., quitting smoking), therapeutic agents (such as bronchodilators which do not address emphysema physiology), long-term oxygen therapy, and surgery (lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails. None of the surgical approaches to treatment of COPD has been widely adopted. Therefore, a large unmet need remains for a medical procedure that can sufficiently alleviate the debilitating effects of COPD and emphysema and is accepted by physicians and patients.

Additionally, respiratory diseases like asthma and COPD are typically treated with inhaled therapeutic agents in order to relieve bronchoconstriction and inflammation in the lung tissue. There are several advantages to administering these therapeutic agents via the inhaled route compared to oral therapy including for example, a faster onset of action, lower therapeutic agent doses and a better efficacy to-safety ratio. therapeutic agent delivery by inhalation is also painless and is more convenient than injectable therapeutic agents and thus patient acceptance and compliance is more likely. However, delivery of therapeutic agents into lung tissue is difficult in asthma and COPD treatment because some patients cannot take the deep breathe necessary to inhale an therapeutic agent aerosol or therapeutic agent powder deep into the lung. Also many of the inhaler device are difficult to operate. Significant and variable amounts of the therapeutic agent are filtered and/or absorbed in the upper respiratory tract. Thus inhaled therapeutic agent delivery is difficult of impossible in the very patients that would benefit most.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a pleurodesis between the visceral and parietal membranes surrounding the passageway as it enters the lung. The pleurodesis prevents air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The artificial aperture into the lung through the chest is referred to herein as a pneumostoma. A pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort (reducing dyspnea), allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing or sealing off a portion of the lung.

In accordance with an embodiment, the present invention provides a pneumostoma management system including a pneumostoma management device and a drug delivery device which interacts with one or more components of the pneumostoma management device to safely and effectively apply therapeutic agent delivery to a pneumostoma. The drug delivery device delivers a therapeutic agent aerosol or therapeutic agent powder deep into the parenchymal tissue of the lung. Therapeutic agents are not lost to filtration in the respiratory tract and thus the delivery is less variable. As a consequence, dosage is more controlled and can be reduced compared to dosage required by other delivery methods such as oral or inhaled.

In accordance with a general embodiment, the present invention provides a drug delivery device and method to safely and effectively apply therapeutic agent delivery to a pneumostoma.

In accordance with one embodiment, the present invention provides a pneumostoma management system which includes a partially-implantable pneumostoma vent, a chest mount and a drug delivery device. The drug delivery device attaches to the chest mount to safely and effectively apply therapeutic agent delivery to a pneumostoma.

In accordance with one embodiment, the present invention provides a pneumostoma management system which includes a partially-implantable pneumostoma vent, a chest mount and drug delivery device. The chest mount is secured to the skin of the patient. The drug delivery device attaches to the chest mount in the absence of the pneumostoma vent.

In accordance with one embodiment, the present invention provides a pneumostoma management system which includes a partially-implantable pneumostoma vent, a chest mount and drug delivery device. The chest mount is secured to the skin of the patient. The partially-implantable pneumostoma vent is placed into a pneumostoma through an aperture in the chest mount. The drug delivery device attaches to the pneumostoma vent while it is mounted in the chest mount.

In accordance with embodiments of the present invention the drug delivery device provides a therapeutic agent in a vapor, aerosolized solution, suspended powder. The therapeutic agent is then introduced into the pneumostoma using a pressure differential between the drug delivery device and the pneumostoma. In some cases a positive pressure may be applied by the drug delivery device. In other cases the drug delivery device remains at or near ambient pressure and the pressure differential is the result of reduced pressure in the pneumostoma during inhalation by the patient.

In accordance with a specific embodiment of the present invention provides a therapeutic agent delivery device which includes: a tube having a proximal end and a distal end adapted to be inserted into a pneumostoma; an aperture in the distal end of the tube adapted to release the at least a portion of the therapeutic agent suspended in a gas into the pneumostoma; a flange connected to the tube to limit insertion of the tube into the pneumostoma; a container selectably connectable to the proximal end of the tube and adapted to include one or more doses of the therapeutic agent; and an actuator which is adapted to release at least a portion of the therapeutic agent and provide the at least a portion of the therapeutic agent suspended in a gas into the proximal end of the tube. Actuation of the actuator provides the therapeutic agent into via the tube into the pneumostoma.

Thus, various systems, components and methods are provided for managing a pneumostoma and thereby treating COPD. Other objects, features and advantages of the invention will be apparent from drawings and detailed description to follow.

BRIEF DESCRIPTION OF THE DRAWINGS

The above and further features, advantages and benefits of the present invention will be apparent upon consideration of the present description taken in conjunction with the accompanying drawings.

FIG. 2C shows a perspective view of a drug delivery device designed to operate with the pneumostoma management device of FIGS. 2A and 2B according to an embodiment of the present invention.

FIG. 2D shows a sectional view of the drug delivery device of FIG. 2C mated with the pneumostoma management device of FIGS. 2A and 2B according to an embodiment of the present invention.

FIG. 2E shows a positioning of a pneumostoma management device and drug delivery device relative to the chest of a patient.

FIG. 2F shows steps for using a drug delivery device according to an embodiment of the present invention.

FIG. 8C shows steps for using a drug delivery device such as shown in FIG. 8A.

FIG. 10A shows a view of a spirometry system for assessing the functionality of a pneumostoma according to an embodiment of the present invention.

FIG. 10B shows a view of a gas analysis system for assessing the functionality of a pneumostoma according to an embodiment of the present invention.

FIG. 10C shows a view of lung imaging system for imaging gas diffusion from a pneumostoma according to an embodiment of the present invention.

FIGS. 10D and 10E show views of a diagnostic device for delivering diagnostic gas to a pneumostoma or sampling gas from a pneumostoma according to embodiments of the present invention.

FIGS. 11A-11C show views of a pneumostoma management device which provides a therapeutic agent to the pneumostoma.

DETAILED DESCRIPTION OF THE INVENTION

Figure 1A:
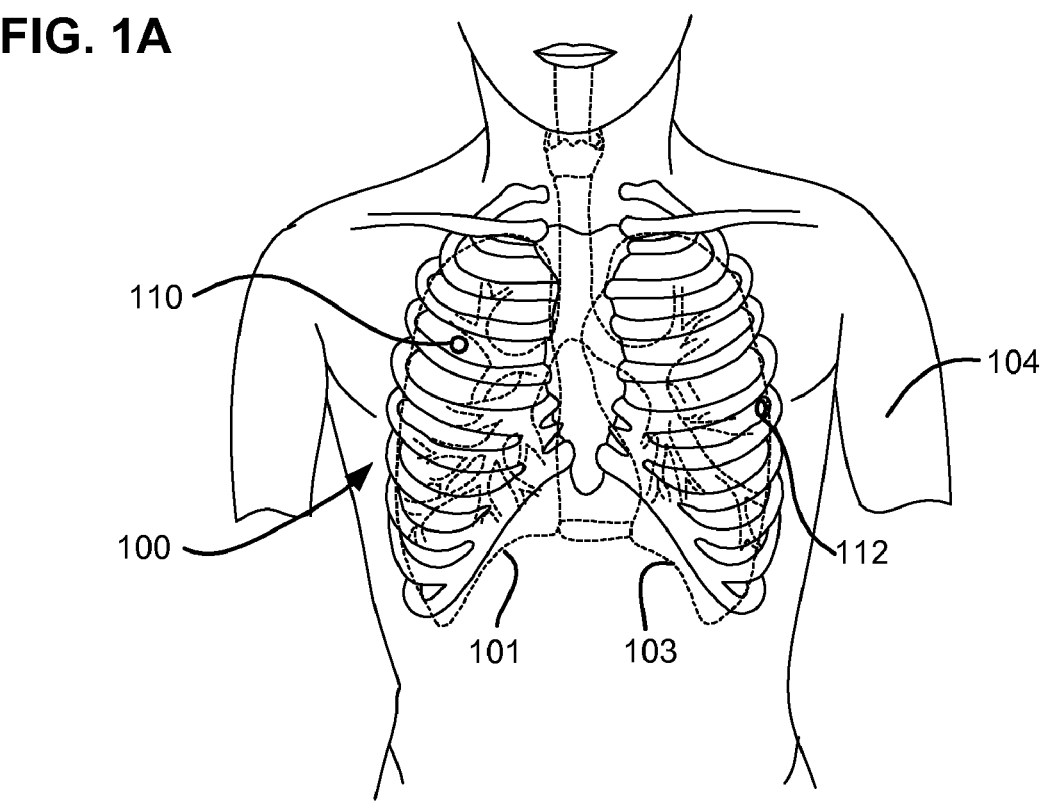
FIG. 1A shows the chest of a patient indicating alternative locations for a pneumostoma that may be managed using the device and methods of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Pneumostoma Formation and Anatomy

FIG. 1A shows the chest of a patient identifying alternative locations for creating a pneumostoma that may be managed using the system of the present invention. A first pneumostoma 110 is shown on the front of the chest 100 over the right lung 101 (shown in dashed lines). The pneumostoma is preferably positioned over the third intercostal space on the midclavicular line. Thus the pneumostoma 110 is located on the front of the chest between the third and fourth ribs. Although the pneumostoma 110 is preferably located between two ribs, in alternative procedures a pneumostoma can also be prepared using a minithoracotomy with a rib resection.

In FIG. 1A a second pneumostoma 112 is illustrated in a lateral position entering the left lung 103 (shown in dashed lines). The pneumostoma 112 is preferably positioned over the fourth or fifth intercostal space under the left arm 104. In general, one pneumostoma per lung is created; however, more or less than one pneumostoma per lung may be created depending upon the needs of the patient. In most humans, the lobes of the lung are not completely separate and air may pass between the lobes.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using adhesives, mechanical sealing and/or pleurodesis. Methods for forming the channel, opening, anastomosis and pleurodesis are disclosed in applicant's pending and issued patents and applications including U.S. patent application Ser. No. 10/881,408 entitled "Methods and Devices to Accelerate Wound Healing in Thoracic Anastomosis Applications," U.S. patent application Ser. No. 12/030,006 entitled "Variable Parietal/Visceral Pleural Coupling," and U.S. Provisional Patent Application Ser. No. 61/038,371 entitled "Surgical Procedure And Instrument To Create A Pneumostoma And Treat Chronic Obstructive Pulmonary Disease" which are incorporated herein by reference in their entirety.

Figure 1B:
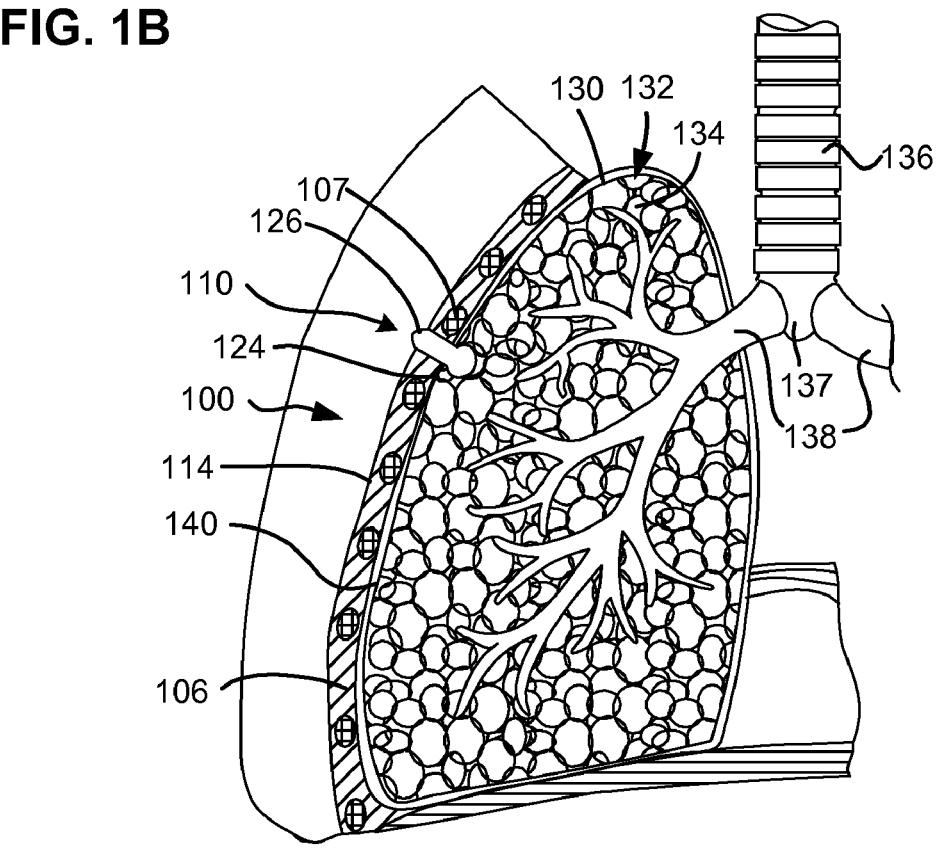
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 138. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100.

Figure 1C:
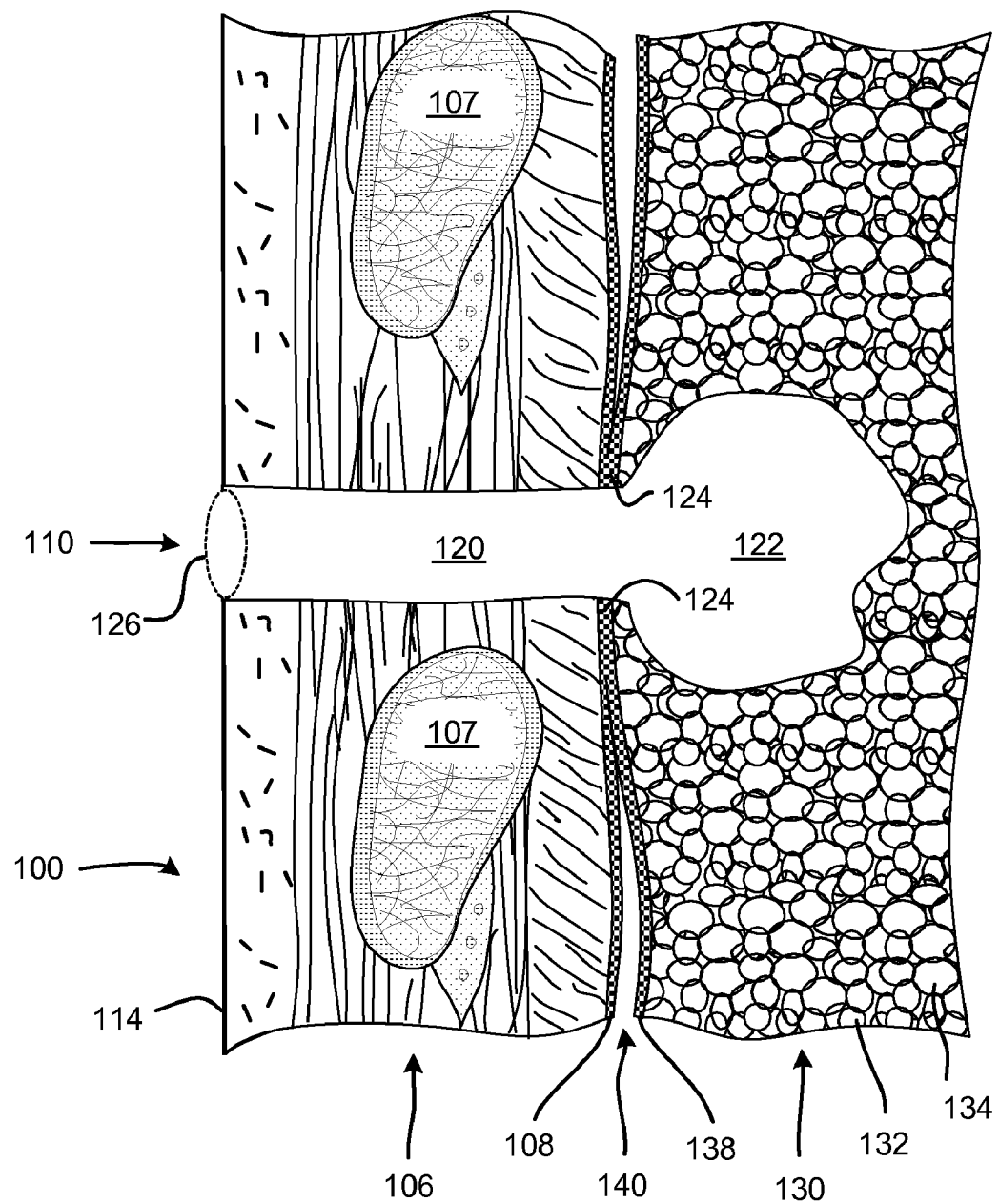
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124 the pleural membranes are fused and/or adhered to one another eliminating the space between the pleural membranes in that region.

An important feature of the pneumostoma is the seal or adhesion surrounding the channel 120 where it enters the lung 130 which may comprise a pleurodesis 124. Pleurodesis 124 is the fusion or adhesion of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, pleurodesis 124 is preferably localized to the region surrounding the channel 120. The pleurodesis 124 surrounding the channel 120 prevents air from entering the pleural cavity 140. If air is permitted to enter pleural cavity 140, a pneumothorax will result and the lung may collapse.

Pleurodesis 124 can be created between the visceral pleura of the lung and the inner wall of the thoracic cavity using chemical methods including introducing into the pleural space irritants such as antibiotics (e.g. Doxycycline or Quinacrine), antibiotics (e.g. iodopovidone or silver nitrate), anti-cancer therapeutic agents (e.g. Bleomycin, Mitoxantrone or Cisplatin), cytokines (e.g. interferon alpha-2β and Transforming growth factor-β); pyrogens (e.g. *Corynebacterium parvum, Staphylococcus aureus* superantigen or OK432); connective tissue proteins (e.g. fibrin or collagen) and minerals (e.g. talc slurry). A pleurodesis can also be created using surgical methods including pleurectomy. For example, the pleural space may be mechanically abraded during thoracoscopy or thoracotomy. This procedure is called dry abrasion pleurodesis. A pleurodesis may also be created using radiotherapy methods, including radioactive gold or external radiation. These methods cause an inflammatory response and or fibrosis, healing, and fusion of the pleural membranes. Alternatively, a seal can be created in an acute manner between the pleural membranes using biocompatible glues, meshes or mechanical means such as clamps, staples, clips and/or sutures. The adhesive or mechanical seal may develop into pleurodesis over time. A range of biocompatible glues are available that may be used on the lung, including light-activatable glues, fibrin glues, cyanoacrylates and two part polymerizing glues. Applicant's copending U.S. patent application Ser. No. 12/030,006 entitled "VARIABLE PARIETAL/VISCERAL PLEURAL COUPLING" discloses methods such as pleurodesis for coupling a channel through the chest wall to the inner volume of the lung without causing a pneumothorax and is incorporated herein by reference for all purposes.

When formed, pneumostoma 110 provides an extra pathway for exhaled air to exit the lung 130 reducing residual volume and intra-thoracic pressure without the air passing through the major natural airways such as the bronchi 138 and trachea 136. Collateral ventilation is particularly prevalent in an emphysematous lung because of the deterioration of lung tissue caused by COPD. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110 thus makes use of collateral ventilation to collect air in cavity 122 and vent the air outside the body via channel 120 reducing residual volume and intra-thoracic pressure and bypassing the natural airways which have been impaired by COPD and emphysema.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Pneumostoma 110 thus achieves many of the advantages sought by lung volume reduction surgery without surgically removing a portion of the lung or sealing off a portion of the lung.

U.S. Pat. No. 7,398,782 titled "Pulmonary Drug Delivery" to Tanaka discusses the local delivery of therapeutic agents directly into the lungs for treating various disease conditions and is incorporated herein by reference. As disclosed herein, a pneumostoma management system in accordance with embodiments of the present invention is advantageous to maintain the patency of a pneumostoma and control flow of materials between the exterior of the patient and the parenchymal tissue of the lung via a pneumostoma. The pneumostoma management system includes a pneumostoma management device and a drug delivery device.

Pneumostoma Management System Including Drug Delivery Device

As described above, a pneumostoma may be created to treat the symptoms of chronic obstructive pulmonary disease. A patient is typically provided with a pneumostoma management device to protect the pneumostoma and keeps the pneumostoma open on a day-to-day basis. In general terms a pneumostoma management device ("PMD") comprises a tube which is inserted into the pneumostoma and an external component which is secured to the skin of the patient to keep the tube in place. Gases escape from the lung through the tube and are vented external to the patient. The pneumostoma management device may, in some, but not all cases, include a filter which only permits gases to enter or exit the tube. The pneumostoma management device may, in some, but not all cases, include a one-way valve which allows gases to exit the lung but not enter the lung through the tube.

Figure 2A:
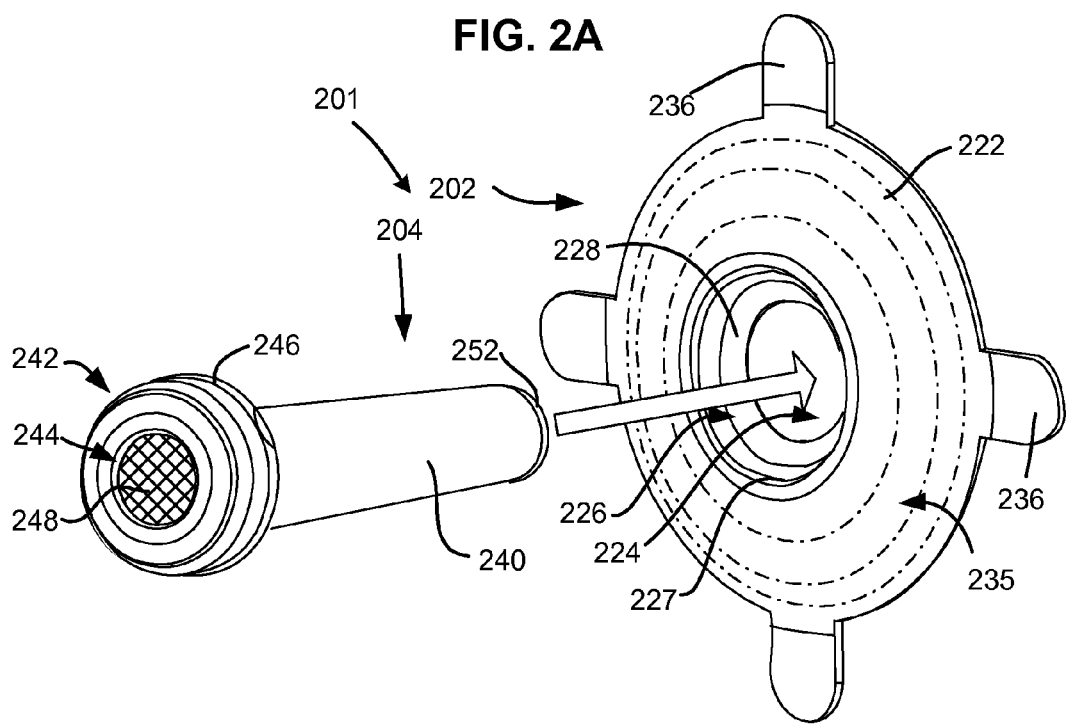
FIG. 2A shows a perspective view of components of a pneumostoma management device according to an embodiment of the present invention.
Figure 2B:
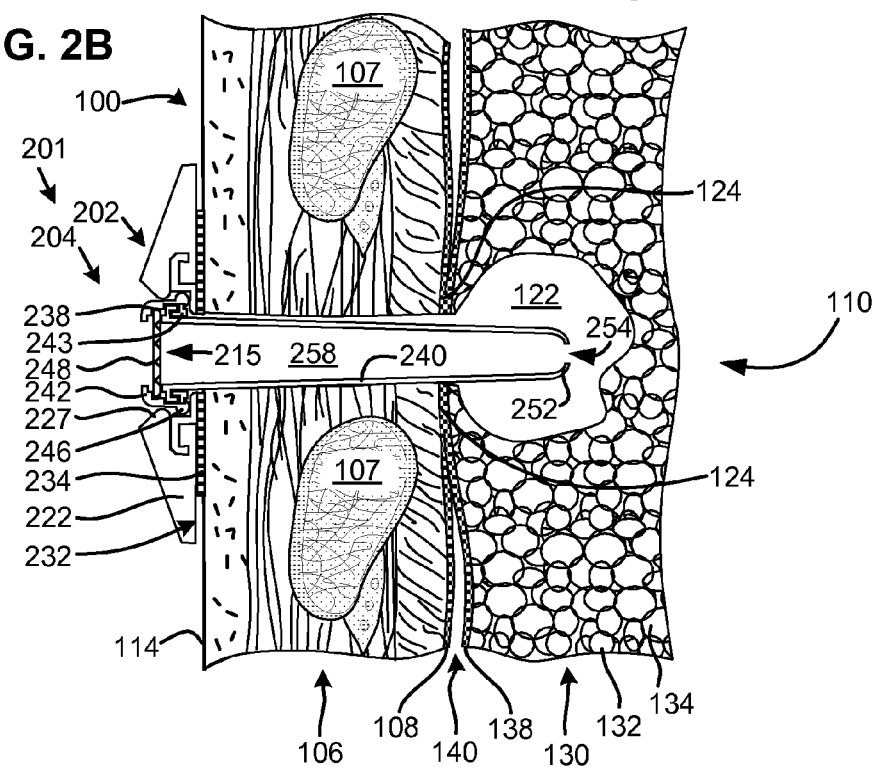
FIG. 2B shows a sectional view of the pneumostoma management device of FIG. 2A partially implanted in a pneumostoma.

FIGS. 2A through 2E illustrate views of a pneumostoma management system including a pneumostoma management device ("PMD") 201 and a drug delivery device 260 in accordance with an embodiment of the present invention. The drug delivery device 260 is shown in FIGS. 2C, 2D and 2E. As shown in FIGS. 2A and 2B, PMD 201 includes a chest mount 202 which may be mounted to the skin of the patient and a pneumostoma vent 204 which is fitted to the chest mount 202. In a preferred embodiment pneumostoma vent 204 is mounted through an aperture 224 in chest mount 202. Chest mount 202 has a first coupling that engages a second coupling of the pneumostoma vent to releasably secure the pneumostoma vent 204 to the chest mount 202. The join between the two components of PMD 201 is engineered to ensure that pneumostoma vent 204 cannot be over-inserted into the lung if it separates from chest mount 202. Applicant's related patent applications referenced above provide further description of pneumostoma management devices and are incorporated herein by reference in its entirety.

Referring now to FIG. 2B, pneumostoma vent 204 includes a tube 240 sized and configured to fit within the channel of a pneumostoma 110. Tube 240 is stiff enough that it may be inserted into a pneumostoma without collapsing. Over time a pneumostoma may constrict and it is one function of PMD 201 to preserve the patency of the channel of the pneumostoma by resisting the natural tendency of the pneumostoma to constrict. Tube 240 of pneumostoma vent 204 preferably comprises an atraumatic tip 252 at the distal end as shown in FIGS. 2A and 2B. (This application uses the terms proximal and distal regarding the components of the pneumostoma management system in the conventional manner. Thus, proximal refers to the end or side of a device closest to the hand operating the device, whereas distal refers to the end or side of a device furthest from the hand operating the device.) Tip 252 may be rounded, beveled or curved in order to reduce irritation or damage to the tissues of the pneumostoma or lung during insertion or while in position. Opening 254 in tip 252 allows the entry of gases from the cavity of the pneumostoma 110 into lumen 258 of tube 240. Tube 240 is optionally provided with one or more side openings (not shown) positioned near tip 252 and/or along the length of tube 240 to facilitate the flow of gas and/or mucous/discharge into lumen 258.

Tube 240 of pneumostoma vent 204 is sufficiently long that it can pass through the thoracic wall and into the cavity of a pneumostoma inside the lung. Pneumostoma vent 204 is not however so long that it penetrates so far into the lung that it might cause injury. The material and thickness of tube 240 of pneumostoma vent 204 is selected such that tube 240 is soft enough that it will deform rather than cause injury to the pneumostoma or lung. Pneumostoma vent 204 has an opening 254 in tip 252 of tube 240. The length of tube 240 required for a pneumostoma vent 204 varies significantly between different pneumostomas. A longer tube 240 is usually required in patients with larger amounts of body fat on the chest. A longer tube 240 is usually required where the pneumostoma is placed in the lateral position 112 rather than the frontal position 110. Because of the variation in pneumostomas, pneumostoma vents 204 are manufactured having tubes 240 in a range of sizes and a patient is provided with a pneumostoma vent 204 having a tube 240 of appropriate length for the patient's pneumostoma. Tube 240 may be from 30 to 120 mm in length and from 5 mm to 20 mm in diameter depending on the size of a pneumostoma. A typical tube 240 may be between 40 mm and 80 mm in length and between 8 mm and 12 mm in diameter. In alternative embodiments, a pneumostoma vent 204 is made with a single length (such as 120 mm) of tube 240 and tube 240 is then cut to the length appropriate for a particular patient. Where a single length tube 240 is provided and subsequently cut to length it is desirable that the tube be shaped such that at each of a plurality of cut points cutting will generate an atraumatic tip. This can be achieved, for example, by including a series of rounded narrow points on tube 240.

Pneumostoma vent 204 includes a cap 242 and a hydrophobic filter 248 over the opening 255 in the proximal end of tube 240. Hydrophobic filter 248 is positioned over the proximal opening 255 into lumen 258. Hydrophobic filter 248 is positioned and mounted such that material moving between lumen 258 and the exterior of pneumostoma vent 204 must pass through hydrophobic filter 248. Hydrophobic filter 248 is preferably designed such to fit into a recess in cap 242. As shown in FIG. 2B, cap 242 comprises a recess 238 into which hydrophobic filter 248 may be fit. Hydrophobic filter 248 may alternatively be fitted into cap 242 using a joint such as a threaded coupling or adhesive or, in some cases, formed integrally with cap 242. Hydrophobic filter 248 may be made from a material such as medical grade GOR-TEX (W. L. Gore & Associates, Inc., Flagstaff, Ariz.). As shown in FIG. 2B, a snap ring 243 locks cap 242 and hydrophobic filter 248 onto the proximal end of tube 240.

Hydrophobic filter 248 serves several purposes. In general, hydrophobic filter 248 controls the passage of solid or liquid material between the lumen 258 and the exterior of cap 242. For example, hydrophobic filter 248 prevents the flow of water into the lumen 258 through proximal opening 255. Thus, a patient using PMD 201 may shower without water entering the lung through the pneumostoma. Hydrophobic filter 248 may also be selected so as to prevent the entry of microbes, pollen and other allergens and pathogens into the lumen 258. Hydrophobic filter 248 also prevents the exit of liquid and particulate discharge from lumen 258 to the exterior of pneumostoma vent 204. This is desirable to prevent contact between liquid and particulate discharge and clothing for example.

Chest mount 202 connects to the proximal end of pneumostoma vent 204. In one embodiment, illustrated in FIGS. 2A and 2B, chest mount 202 comprises a flange 222 and an aperture 224. The aperture 224 is adapted and configured to receive the pneumostoma vent 204. Chest mount 202 is designed to have a smooth surface and a low profile so it is comfortable for the patient to wear. Chest mount 202 should be designed so as not to snag on the patient's clothing or to restrict motion of the patient's arm (if placed in a lateral pneumostoma 112). Flange 222 is significantly wider than pneumostoma vent 204. Flange 222 thus comprises a contact surface 232 which contacts the skin of the patient surrounding the pneumostoma and positions the aperture 224 over the opening of the pneumostoma. Flange 222 is designed such that it is sufficiently flexible that it can conform to the surface of the chest. Contact surface 232 is also provided with a pad of biocompatible adhesive 234, such as a hydrocolloid adhesive, for securing flange 222 to the skin of the patient. The adhesive 234 may be protected by a protector sheet that is removed prior to use of flange 222. Adhesive 234 should be selected so as to secure flange 222 to the chest of the patient in the correct position relative to the pneumostoma without causing undue irritation to the skin of the patient. The adhesive need not create an air tight seal between flange 222 and the skin of the patient. Suitable adhesive pads are available commercially from Avery Dennison (Painesville, Ohio).

Referring again to FIGS. 2A and 2B, cap 242 is attached to the proximal end of tube 240. Hydrophobic filter 248 is sandwiched between cap 242 and tube 240. An opening 244 in cap 242 communicates with the lumen 258 of tube 240 via hydrophobic filter 248. As shown in FIGS. 2A and 2B, cap 242 comprises a lip 246 which releasably engages lip 227 of recess 226 of flange 222 to secure pneumostoma vent 204 within the recess 226 of flange 222. Lip 246 forms a coupling element of pneumostoma vent 204 that cooperates with recess 226 to releasably secure pneumostoma vent 204 into chest mount 202 with tube 240 positioned through aperture 224.

Referring again to FIGS. 2A and 2B, flange 222 is generally circular but is provided with one or more tabs 236 to facilitate application and removal of flange 222 from the skin of the patient. Chest mount 202 comprises an aperture 224 through which tube 240 of pneumostoma vent 204 may be inserted. Flange 222 is slightly convex on the upper surface 235. Flange 222 includes a recess 226 into which cap 242 of pneumostoma vent 204 may be press fit. Flange 222 is thick enough in the region of aperture 224 to receive the cap 242 of pneumostoma vent 204 so that the cap of pneumostoma vent 204 is flush with the upper surface 235 of flange 222. Recess 226 forms a coupling adapted to releasably secure the cap 242 of pneumostoma vent 204 into flange 222. Recess 226 has a lip 227 to releasably secure the cap 242 of pneumostoma vent 204 into flange 222. However, other couplings may be used to releasably secure pneumostoma vent 204 to chest mount 202 including clips, pins, snaps, catches, threaded joints, temporary adhesive and the like.

In a preferred embodiment, an aperture plate 228 is embedded in the conformable polymer of flange 222. The aperture plate 228 defines aperture 224 of chest mount 202. Aperture plate 228 is made of a stiffer, less compliant material than flange 222 in order that the dimensions of aperture 224 are tightly controlled. Aperture plate 228 is stiff enough that the size and shape of aperture 224 remains stable even under any reasonably possible application of force to chest mount 202. It should be noted that the outer diameter of each of snap ring 243, hydrophobic filter 248, flange 241 and cap 242 is larger than the diameter of aperture 224 of aperture plate 228. Thus, snap ring 243, hydrophobic filter 248, flange 241 and cap 242 cannot pass through aperture 224 into the pneumostoma 110. Distal tip 252 of tube 240 and the body of tube 240 are small enough to pass through aperture 224 however, flange 241 and/or cap 242 serve to limit the passage of tube 240 through aperture 224. These safety features prevent unsafe entry of any of the components of pneumostoma vent 204 into pneumostoma even in the unlikely event of damage to the device. Likewise all the components of the chest mount 202 such as flange 222 and aperture plate 224 are significantly larger than the aperture of a pneumostoma thus precluding passage of any component of the chest mount 202 into a pneumostoma even in the unlikely event of damage to the device.

Referring now to FIGS. 2C and 2D which show views of a drug delivery device 260 designed to be used in conjunction with PMD 201 of FIGS. 2A and 2B as part of a pneumostoma management system. FIG. 2C shows a perspective view of drug delivery device 260. FIG. 2D shows a sectional view through drug delivery device 260 of FIG. 2C when mounted in a chest mount 202. As shown in FIGS. 2C and 2D, drug delivery device 260 includes a therapeutic agent dispenser 262, a coupling 264 and a tube 266. Drug delivery device 260 is configured such that tube 266 may be inserted through aperture 224 of chest mount 202 into pneumostoma 110. Tube 266 is sufficiently long to enter the pneumostoma but is not so long that it might cause injury to the pneumostoma. Coupling 264 is designed such that it is too large to pass through aperture 224 of chest mount 202 thereby preventing further insertion of tube 266 into pneumostoma 110. Coupling 264 may optionally be provided with a feature such as a lip 265 for releasably engaging lip 227 of recess 228 of chest mount 202. A range of drug delivery devices may be manufactured each having a size appropriate for a different pneumostoma.

To simplify manufacture, drug delivery device 260 may be designed to use some components in common with pneumostoma vent 240. For example, the range of tubes 240 of the pneumostoma vent may be used as tube 266 of drug delivery device 260. Alternatively it may be preferable to make drug delivery device with only one size of tube 266 and thus the shortest of tubes 240 may be selected for use in drug delivery device 260. In some embodiments, the snap ring 243 may also be a shared component 264. The distal end of coupling 264 is shaped similarly to cap 242 and thus the snap ring 243 can join tube 266 to coupling 264 in the same manner as tube 240 is coupled to cap 242. Also the exterior surface of the distal end of coupling 264 engages chest mount 202 in the same way as cap 242. This simplifies the manufacturing and regulatory process for drug delivery device 260.

Therapeutic agent dispenser 262 includes a mechanism for providing an aerosol, mist or powder in suspended in a propellant gas under sufficient positive pressure to enter the lung through the tube. The therapeutic agent dispenser preferably provides positive pressure to push the therapeutic agent into the pneumostoma. Suitable therapeutic agent dispenser mechanisms for providing metered doses of therapeutic agents in a propellant gas are known. Suitable therapeutic agent dispensers include therapeutic agent dispensing mechanisms found in nebulizers, ultrasonic nebulizers, metered dose inhalers and dry powder inhalers. Dry powder therapeutic agent dispensers deliver a fine microcrystalline suspension of therapeutic agent. In the example shown in FIGS. 2C, 2D a pressurized canister 268 is received in sleeve 270. The outlet valve 269 of canister 268 engages a fixture 272 in the bottom of sleeve 270. When the user pushes canister 268 down into sleeve 270, fixture 272 activates valve 269 to release a metered dose of therapeutic agent in a propellant gas. The therapeutic agent and propellant gas pass through a channel 274 in fixture 270 and are ejected into and through tube 266 as shown by arrow 276.

Note that in some embodiments it is unnecessary for therapeutic agent dispenser 262 to provide a propellant gas at positive pressure to introduce the aerosol, mist or powder into the lung through the pneumostoma. In some embodiments the therapeutic agent dispenser 262 provides the therapeutic agent/gas mixture at or near ambient pressure. Reduced pressure in the pneumostoma during inhalation by the patient creates a pressure differential which sucks the therapeutic agent suspended in air/gas into the pneumostoma.

FIG. 2E illustrates the positioning of drug delivery device 260 over pneumostoma 112 of FIG. 1A. In a preferred embodiment, the chest mount 202 remains attached for up to a week thereby avoiding irritation of the skin caused by daily attachment and removal of a mount. Chest mount may be positioned by the patient by manual alignment of the aperture 224 of chest mount 202 with the aperture of the pneumostoma 112. To use drug delivery device 260, chest mount 202 is first positioned over a pneumostoma and secured with adhesive to the skin of the patient. Alternatively a pneumostoma vent or an alignment tool may be used to align the chest mount. Drug delivery device 260 is then inserted through the aperture in the chest mount until it engages the chest mount 202. As shown in FIG. 2E, the drug delivery device 260 is inserted through chest mount 202 after pneumostoma vent 204 has been removed. Drug delivery device 260 is then operated to supply the aerosolized or dry powder therapeutic agent directly to the parenchymal tissue of the lung through pneumostoma 112 by operation of therapeutic agent dispenser 262 either by the patient, caregiver or medical practitioner.

FIG. 2F shows an example of a method of using a drug delivery device according to embodiments of the present invention. The method may be described in instructions for use provided to the patient with the drug delivery device. At step 280, the patient adjusts the pneumostoma management device. Depending on the operation of the drug delivery device, this step may involve, for example, removing a component of the pneumostoma vent such as the filter; removing the entire pneumostoma vent; or removing the entire pneumostoma management device. At step 282, the patient positions the drug delivery device in the pneumostoma. In some embodiments this step will involve connecting the pneumostoma management device to a tube already positioned in the pneumostoma. At step 484, the patient loads a dose of the therapeutic agent into the drug delivery device. In some cases, the therapeutic agent is provided in single dose containers and thus this will involve loading a single dose package or indexing a package containing multiple singe dose containers to a full container. In other cases, the therapeutic agent will be in a multiple-use container, such as a pressurized metered dose canister and it will be unnecessary for the patient to load a therapeutic agent dose unless the container is empty. The drug delivery device is now prepared for operation.

In a typical therapeutic agent delivery operation the patient will first exhale through the nose/mouth at step 285 immediately prior to actuating the drug delivery device. At step 286 the drug delivery device is actuated to mix the therapeutic agents (aerosol, gas or dry powder) in the propellant/air. In some embodiments this mixing step requires a relatively high air speed/pressure. It may be undesirable for this airspeed/pressure to be applied to the pneumostoma and thus the location of mixing step 286 may be separated by features to reduce the airspeed/pressure distance before the mixture reaches the pneumostoma. Such features may include, for example, space, volume, baffles and the like. At step 288 application of positive pressure is used to propel the mixture of therapeutic agent and propellant into the pneumostoma and/or through the pneumostoma into the lung. The positive pressure applied at this step may be substantially less than the pressure used at step 286. The positive pressure may be supplied by a different mechanism or by a modulation of the same mechanism. Steps 286 and 288 may be combined in one step for example where the pressure is modulated by the mechanics of the device such that a higher local pressure is available in one part of the device to mix the agent but is reduced by the time it reaches the pneumostoma. Note that in some embodiments it is unnecessary for the therapeutic agent dispenser to provide propellant gas at positive pressure to introduce the aerosol, mist or powder into the lung through the pneumostoma. In some embodiments the drug delivery device remains at or near ambient pressure and reduced pressure in the pneumostoma during inhalation by the patient creates a pressure differential which sucks the aerosol, mist or powder suspended in air/gas into the pneumostoma.

At step 290, air is introduced through the pneumostoma to aid distribution of the therapeutic agent through the lung tissue by collateral ventilation. Step 290 is optional and may in some cases be combined with step 288. In some cases step 290 may be achieved by the patient "inhaling" through the pneumostoma in which the patient expands the ribcage thereby creating a negative pressure in the chest to draw air in through the pneumostoma. In some circumstances this "inhalation" through the pneumostoma may be enhanced by obstructing the nose and mouth while expanding the ribcage. However, step 290 may not be necessary and a therapeutic agent may be efficiently distributed from the pneumostoma through parenchymal tissue of the lung by collateral ventilation without the need for additional intake of air through the pneumostoma.

At step 292, the patient optionally holds their breath for a time prior to exhaling, such as 10 to 15 seconds. This step may not be necessary for therapeutic agents delivered into the pneumostoma. Because the therapeutic agent was not delivered through the natural airways, it will not be rapidly exhaled through the natural airways. Indeed, in some cases breathing normally (while obstructing the pneumostoma) while cause rapid distribution of the therapeutic agent through the lung with little loss of therapeutic agent due to exhalation. In some case it may be advantageous to provide a slight positive pressure of air to the pneumostoma after delivery of the therapeutic agent to promote diffusion of the therapeutic agent through the lung. Steps 284 and 292 may be repeated a number of times if necessary to deliver multiple doses of therapeutic agent as shown by dashed arrow 294.

It may be desirable to leave the drug delivery device in place for a period after delivery of therapeutic agent to prevent the agent from being ejected through the pneumostoma. After the therapeutic agent has been delivered, the drug delivery device is removed from the pneumostoma at step 296. In some cases the drug delivery device may be detached from the pneumostoma vent of chest mount. At step 298, the pneumostoma management device is replaced into the pneumostoma. Alternatively, any removed components of the pneumostoma management device are reattached. Any or all of the above steps may be performed and/or controlled by a physician or caregiver instead of the patient. The therapeutic agent delivery steps may be repeated according to a particular dosing schedule or as needed depending on the therapeutic agent and/or physician's instructions.

Therapeutic Agents for Delivery Through a Pneumostoma

The present invention provides a drug delivery device which delivers a therapeutic agent into the lung 130 without passing through the mouth and the major natural airways such as the bronchi 138 and trachea 136. For inhaled therapeutic agents, a significant fraction of the therapeutic agent may be deposited in the upper respiratory tract and may cause unwanted side effects. For example, inhalation of corticosteroids to reduce inflammation, can suppress the immune system in the mouth leading to infections. Additionally, the amount of therapeutic agent reaching the lung can vary depending upon the abilities of the patient to use the inhaler. In the present invention a much larger fraction of the therapeutic agent is delivered directly to the lung. Moreover, the therapeutic agent is circulated in the lung, at least in part, using collateral ventilation through the connective tissue between the alveoli 134. Collateral ventilation is particularly prevalent in an emphysematous lung because of the deterioration of lung tissue caused by COPD. Collateral ventilation may distribute the therapeutic agent through pathways that include the interalveolar pores of Kohn, bronchiole-alveolar communications of Lambert, and interbronchiolar pathways of Martin. This may provide better and/or more direct access to the damaged tissues of the lung than is possible through the natural airways.

The dosage of a particular therapeutic agent required to be delivered by the pneumostoma will, in many cases, be significantly less than the dosage that would be required to be delivered by the natural airways for the same therapeutic effect. The lower dose can be used because the therapeutic agent delivered through the pneumostoma is not trapped in the natural airways by the body's natural defenses against particulates in the air. Not only does a higher fraction of therapeutic agent reach the lung tissue but the variability of drug delivery is also less. The lower dosage required for delivery through the pneumostoma is advantageous as it reduces the amount and therefore cost of the therapeutic agent, reduces side effects to the patient, and renders dosing more consistent.

As used herein, therapeutic agents may be solid, liquid (including solutions and suspensions), and/or gas. In general, there are three types of therapeutic agents that may be delivered using the methods and devices of the present invention: therapeutic agents to treat the tissues of the pneumostoma; therapeutic agents to treat tissue within the lung; and therapeutic agents to treat diseases that are not lung-specific.

For treatment of the pneumostoma, the therapeutic agent has the shortest distance to travel. The therapeutic agent is distributed utilizing absorption and diffusion through the pneumostoma and into lung parenchymal tissue adjacent the pneumostoma. Parameters of the delivery may be selected so that the therapeutic agent is selectively absorbed in the immediate vicinity of the pneumostoma. For example, the droplet/powder size may be increased and/or the amount of propellant decreased to reduce transport of the agent away from the pneumostoma. Therapeutic agents for treating the pneumostoma may include, without limitation, agents to promote healing, agents to reduce scarring, agents to maintain the patency of the pneumostoma; agents to prevent infection; agents to maintain the collateral ventilation into/from the pneumostoma. Suitable therapeutic agents may have an anti-inflammatory and/or antiproliferative and/or spasmolytic and/or endothelium-forming effect, so that the functionality of the pneumostoma is maintained. Suitable therapeutic agents may include, for example, steroidal compounds; antibiotics and retinoic acid.

For treatment of the tissue within the lung, the therapeutic agent is distributed utilizing collateral ventilation, absorption and diffusion through the lung tissues. Parameters of the delivery may be selected so that the therapeutic agent is readily transported via collateral channels. For example, the droplet/powder size may be decreased and/or the amount of propellant increased to enhance transport of the agent through collateral channels. The therapeutic agents can include agents which work directly on the bronchiole mucosa and smooth muscle when used properly. For example bronchospasm is a major component COPD which limits airflow. Bronchospasm can be relieved by bronchodilator therapeutic agent including, without limitation, beta-2 adrenergic agonists and anticholinergic therapeutic agents. The following therapeutic agents may be particularly suitable as they are commonly used for treatment of COPD: albuterol, chromolyn, salbuterol, metaproterenol, pirbuterol, salmeterol, formoterol, ipratropium, tiotropium, flucatisone, budesonide, flunisolide, beclamethasone, triamcinolone, mometasone or combinations and analogs thereof.

Other agents suitable for treating the lung tissue include, without limitation: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (inaperturethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), anti-asthmatics, nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); silver compound and protease inhibitors.

The method and devices of the present invention are also useful for delivery of therapeutic agents for treating diseases which are not lung-specific. In such cases, the pneumostoma and lung tissue are utilized as absorption surfaces through which the agent may enter the blood stream for systemic distribution to all of the tissues of the body. Parameters of the delivery may be selected so that the therapeutic agent is readily transported via collateral channels in order to be absorbed over a large surface area additionally, the therapeutic agent should be selected/treated such that it may readily pass into the bloodstream. In one example, insulin may be delivered to the patient through the pneumostoma. The insulin is absorbed within the lung and passes into the blood where it is effective to control blood sugar levels. The insulin delivery should be more rapid and reliable than inhaled or oral insulin delivery methods and avoid the need for injection of insulin.

Other suitable pharmaceutically-active substances for delivery through the pneumostoma include, without limitation: amino acids, anabolics, analgesics and antagonists, anaesthetics, anti-adrenergic agents, anti-atherosclerotics, antibacterials, anticholesterolics, anti-coagulants, antidepressants, antidotes, anti-emetics, anti-epileptic therapeutic agents, anti-fibrinolytics, anti-inflammatory agents, antihypertensives, antimetabolites, antimigraine agents, antimycotics, antinauseants, antineoplastics, anti-obesity agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media, radiopaque agents and radioisotopes), electrolytes, enzymes, enzyme inhibitors, ferments, ferment inhibitors, gangliosides and ganglioside derivatives, hemostatics, hormones, hormone antagonists, hypnotics, immunomodulators, insulin, immunostimulants, immunosuppressants, minerals, muscle relaxants, neuromodulators, neurotransmitters and neurotrophins, osmotic diuretics, parasympatholytics, para-sympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, saccharides, polysaccharides, glycoproteins, hyaluronic acid, and any excipient that can be used to stabilize a proteinaceous therapeutic.

The therapeutic agent dosage will depend upon factors including: the intended location of action of therapeutic agent, the efficiency of distribution of the therapeutic agent, the repeatability of distribution of the therapeutic agent and the amount/concentration of therapeutic agent necessary for therapeutic action. In general the dosage will be first determined during trials of the therapeutic agent on a population. Based upon trials, the physician will determine a dose for a particular patient and prescribe the therapeutic agent and/or delivery protocol accordingly. For example a physician may prescribe larger sized doses of therapeutic agent or a larger number of repetitions of dosages to achieve the same total dosage. Therapeutic agent delivery through the pneumostoma requires therapeutic agents to travel a shorter pathway than inhaled therapeutic agent leading to more efficient and repeatable distribution. Additionally, the therapeutic agent is not subject to breakdown by stomach acid and enzymes as it is when delivered via the oral route. The increased efficiency and repeatability of distribution means that, in general, less therapeutic agent need be included per dose, enhancing control of the therapeutic effects and reducing side-effects.

Propellants for Delivery of Therapeutic Agents Through a Pneumostoma

In the past, chlorofluorocarbons were the primary substances used as propellants in aerosols. Since 1978, the use of chlorofluorocarbon-emitting products in the United States has been curtailed sharply because of their adverse effects upon the ozone layer. The pharmaceutical industry has developed alternative propellants such as hydro-fluoroalkanes which are the new environmentally-friendly chemical propellants. Both chlorofluorocarbons and hydro-fluoroalkanes are suitable chemical propellants for use in the present invention.

Lower pressures and flow rates are required for direct delivery of therapeutic agents to the lung in embodiments of the present invention than are needed for delivery via inhalation. This allows for the use of air at slight positive pressures to be used to propel the therapeutic agent a short distance into the lung. As used herein propellant should be taken to include chemical propellants as well as gases at positive pressure. The air may be provided by a fan, pump, cylinder or bag, for example which may be operated by a powered actuator or manually. The pressure of propellant supplied by the device should be carefully controlled/regulated to ensure that it does not damage the pneumostoma or lung tissue. In some cases, a safety valve may be provided to allow gas to escape the pneumostoma or drug delivery device if the pressure supplied to the pneumostoma exceeds a safe threshold. Note that in some embodiments the drug delivery device remains at or near ambient pressure and reduced pressure in the pneumostoma during inhalation by the patient creates a positive pressure differential which sucks the aerosol, mist or powder suspended in air/gas into the pneumostoma.

Diagnostic Agents for Delivery Through a Pneumostoma

In alternative embodiments, a diagnostic agent rather than a therapeutic agent may be delivered through the pneumostoma. The diagnostic agent may be useful for diagnosing lung function in general and pneumostoma function in particular. For example, polarized Helium-3 may be utilized to enhance nuclear magnetic resonance/magnetic resonance imaging of the lung (analogous to the way contrast agents enhance X-ray imaging). Polarized helium-3 may be produced with lasers and the magnetized pressurized gas may be stored for several days. When inhaled, the gas can be imaged with an MRI-like scanner which produces breath by breath images of lung ventilation, in real-time. Polarized helium-3 may thus, be used to visualize airways in static or dynamic fashion. Introducing a controlled amount of Helium-3 through the pneumostoma and imaging the diffusion of Helium-3 into the lung over time may be utilized to evaluate the function of the pneumostoma and the prevalence of collateral ventilation pathways connecting the pneumostoma to the remainder of the lung. Such evaluation may be useful in determining the location and/or desirability of additional pneumostomas. A source of polarized Helium-3 may be connected to the PMD and/or pneumostoma using one of the several techniques and mechanism described herein.

In an alternative method, a diagnostic gas is introduced through the pneumostoma and the gas is measured as it is exhaled through the natural airways. The diagnostic gas may for example be a gas mixture such as DLCO gas used in diffusion spirometry (which nominally consists of 10% helium, 3000 ppm carbon monoxide and the balance air). The difference between gas concentrations in the gas introduced through the pneumostoma and exhaled by the patient is measured and factored with inspired gas volume and other parameters to calculate factors related to collateral ventilation and pneumostoma function. During exhalation, a portion of the breath is collected in a sample collection system and then assessed using a helium sensor, gas chromatograph. The time course of exhalation of the diagnostic gas is indicative of factors such as pneumostoma functionality and collateral ventilation without the need for magnetic resonance imaging.

Alternative Drug Delivery Devices

Figure 3A:
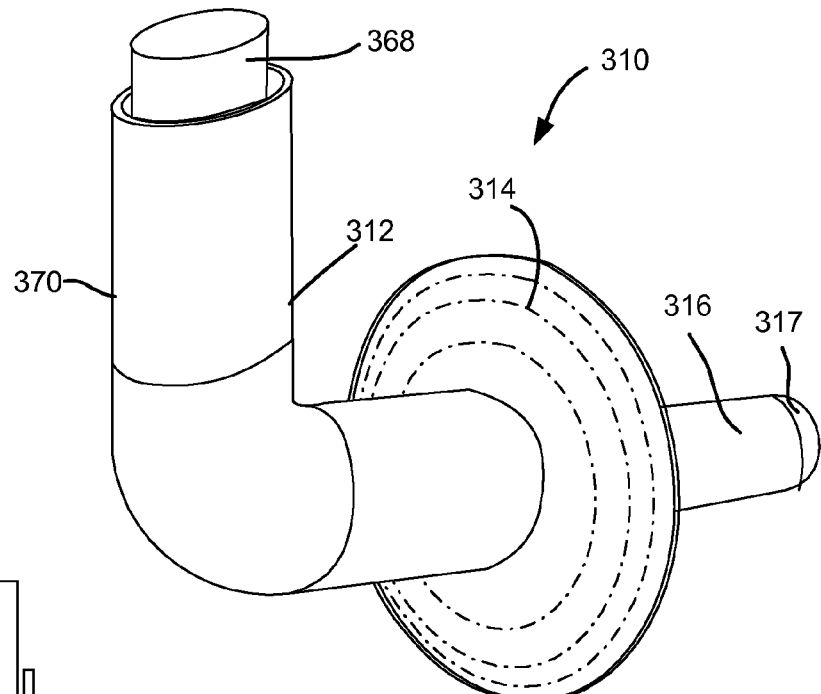
FIG. 3A shows a perspective view of an alternative drug delivery device according to an embodiment of the present invention.
Figure 3B:
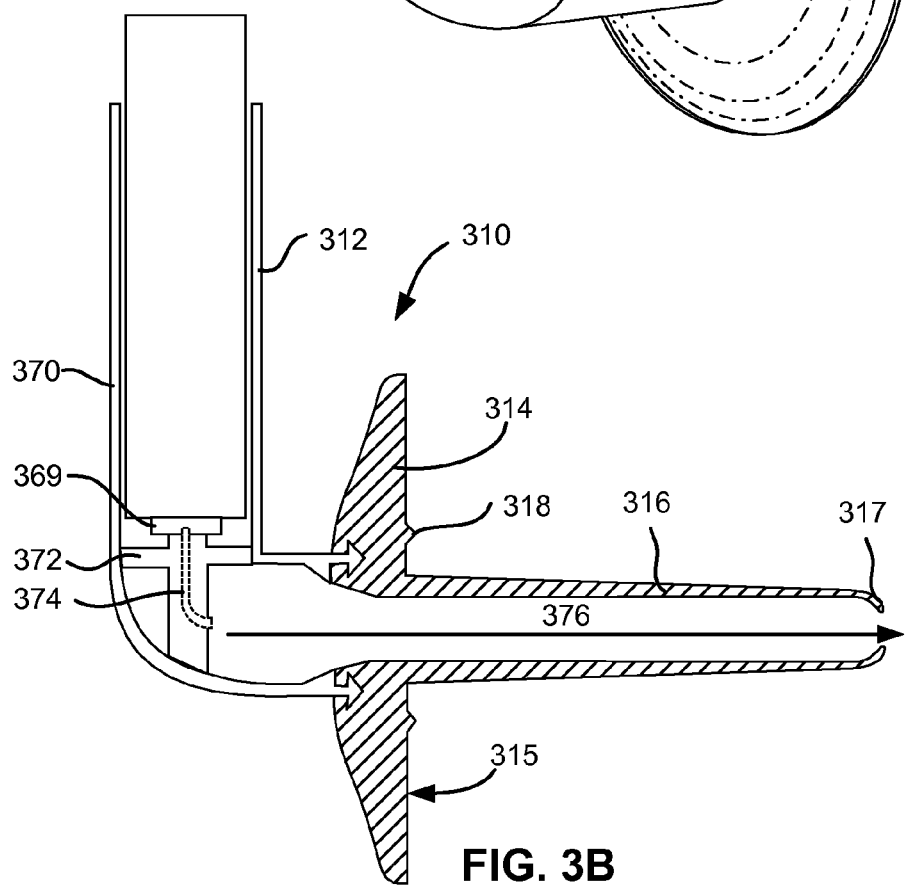
FIG. 3B shows a sectional view of the drug delivery device of FIG. 3A.

FIGS. 3A and 3B show an alternative drug delivery device to deliver therapeutic agents to a pneumostoma. FIG. 3A shows a perspective view of an alternative drug delivery device 310. FIG. 3B shows a sectional view of the drug delivery device 310. As shown in FIGS. 3A and 3B, drug delivery device 310 includes a therapeutic agent dispenser 312 attached to a flange 314 which is attached to a tube 316. Flange 314 is significantly larger than the diameter of tube 316. Flange 314 is too large to enter a pneumostoma and thus acts as a stop to prevent further insertion of tube 316 when flange 314 makes contact with the skin of the patient's chest. The contact surface 315 of flange 314 may also be used to make a temporary seal surrounding the pneumostoma so that when applying therapeutic agent delivery to the pneumostoma there is reduced leakage of propellant/therapeutic agent around tube 316. Contact surface 315 and/or tube 316 may be provided with surface features to enhance the formation of a temporary seal between flange 314 and the skin of the chest. An annular ridge 318 is shown in FIG. 3B.

Tube 316 extends far enough past flange 314 that it can pass through the thoracic wall and into the pneumostoma. Tube 316 is not however so long that it may cause injury to the pneumostoma or lung. The length of a pneumostoma varies significantly between different patients. A longer tube 316 may be desirable for a longer pneumostoma. Because of the variation in pneumostomas, drug delivery devices 310 may be manufactured having tubes 316 in a range of sizes. A patient may then be provided with a drug delivery device 310 having a tube 316 of appropriate length for the patient's pneumostoma. Tubes 316 may be from 30 to 120 mm in length and from 5 mm to 20 mm in diameter depending on the size of a pneumostoma. A typical tube 240 may be between 40 mm and 80 mm in length and between 8 mm and 12 mm in diameter. In alternative embodiments a drug delivery device may be made with a tube 316 of a single length (such as 120 mm) which is then cut to the length appropriate for a particular patient. Alternatively a fixed short tube may be used for all patients—such a tube will occupy at least the entrance to the pneumostoma and therefore suffice for the delivery of the therapeutic agent. Tube 316 of drug delivery device 310 preferably has an atraumatic tip 317 at the distal end to prevent injury and/or irritation to the pneumostoma during insertion.

As shown in FIGS. 3A and 3B, flange 314 and tube 316 of drug delivery device 310 are made in one piece and permanently attached to therapeutic agent dispenser 312. A join is shown between therapeutic agent dispenser 312 and flange 314 because it is preferred that a stiffer material be used for therapeutic agent dispenser 312 and a more flexible material be used for tube 316 which enter the pneumostoma. The parts may be formed separately and then joined by welding, gluing or otherwise bonding/connecting. Note that, for safety reasons, each of the components of therapeutic agent dispenser is preferably too large to fit through tube 316. This prevents aspiration of any of the components into the lung even in the event of damage to drug delivery device 310. As shown in FIG. and 3B a pressurized canister 368 is received in sleeve 370. The outlet valve 369 of canister 368 engages a fixture 372 in the bottom of sleeve 370. When the user pushes canister 368 down into sleeve 370, fixture 372 activates valve 369 to release a metered dose of therapeutic agent in a propellant gas. The therapeutic agent and gas passes through a channel 374 in fixture 372 and are ejected into and through tube 316 as shown by arrow 376.

Figure 4A:
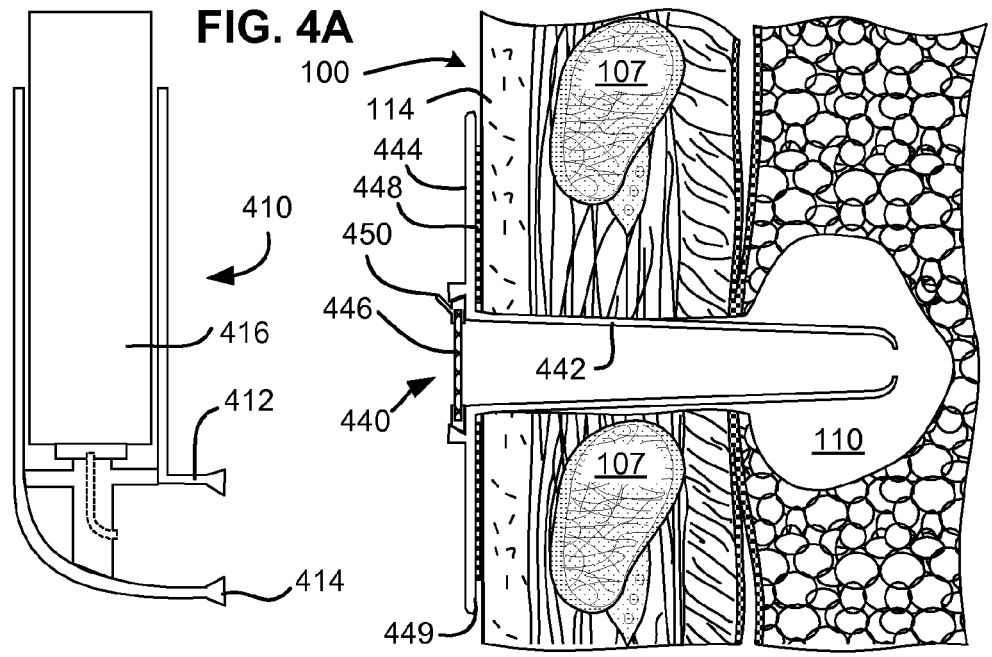
FIGS. 4A and 4B show sectional views of an alternative drug delivery device according to an embodiment of the present invention.
Figure 4B:
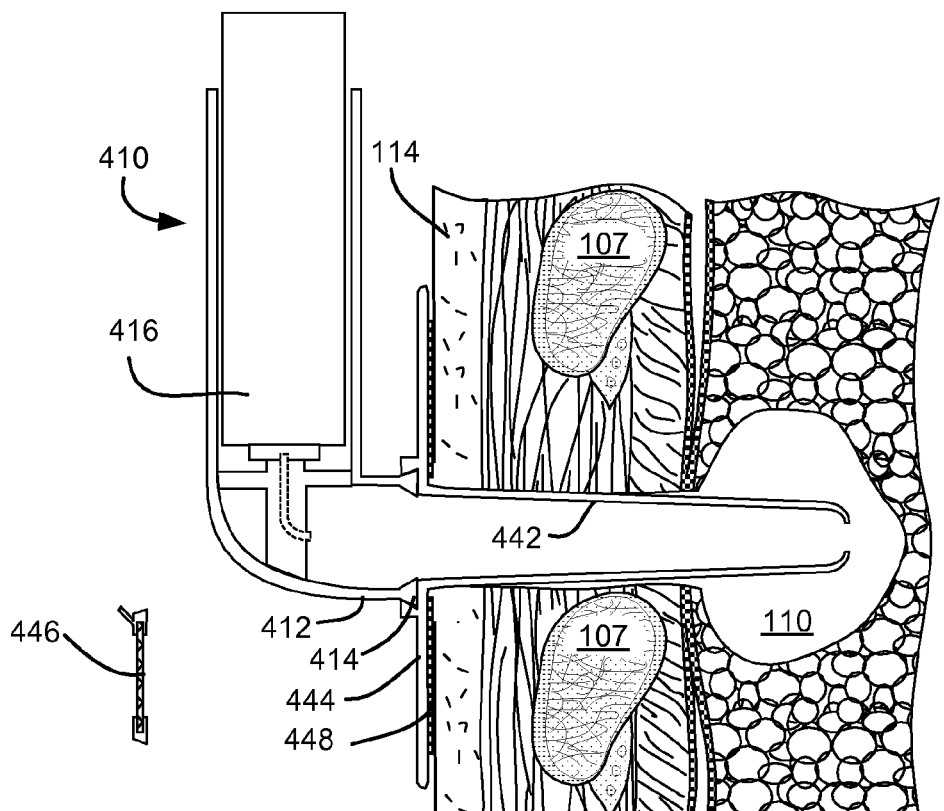

FIGS. 4A and 4B show an alternative drug delivery device 410 to supply a therapeutic agent in/through a pneumostoma. The drug delivery device 410 operates in conjunction with a pneumostoma management device (PMD) 440 located within a pneumostoma 110. In the PMD 440 of FIGS. 4A and 4B, tube 442 is formed in one piece with (or permanently attached to) a flange 444. PMD 440 has a hydrophobic filter 446 press fit into the proximal end of tube 442 and has a biocompatible adhesive 448 on the contact surface 449 of flange 444 for releasably securing flange 444 to the skin 114 of the patient's chest 100. As shown in FIG. 4D, drug delivery device 410 has a mating section 412, having a mating surface 414 designed to mate and make a temporary seal with the exterior surface of flange 444.

Drug delivery device 440 is utilized with PMD 440 while the tube 442 of PMD 440 is within pneumostoma 110. As shown in FIG. 4A, to use drug delivery device 410, hydrophobic filter 446 is first removed by pulling on tab 450. Mating surface 414 of mating section 412 is then placed against flange 444. In this embodiment, mating section 412 fits in the space left by the removal of hydrophobic filter 446 as shown in FIG. 4B. When mating section 412 has formed a temporary seal with flange 444, therapeutic agent dispenser 416 is operated to dispense the therapeutic agent through the tube 442 of PMD 440 into the pneumostoma 110. After dispensing the therapeutic agent, the drug delivery device 410 is removed and the hydrophobic filter 446 is press fit into the proximal end of the tube 442. Alternatively PMD 440 may be replaced with a new PMD 440.

Figure 5A:
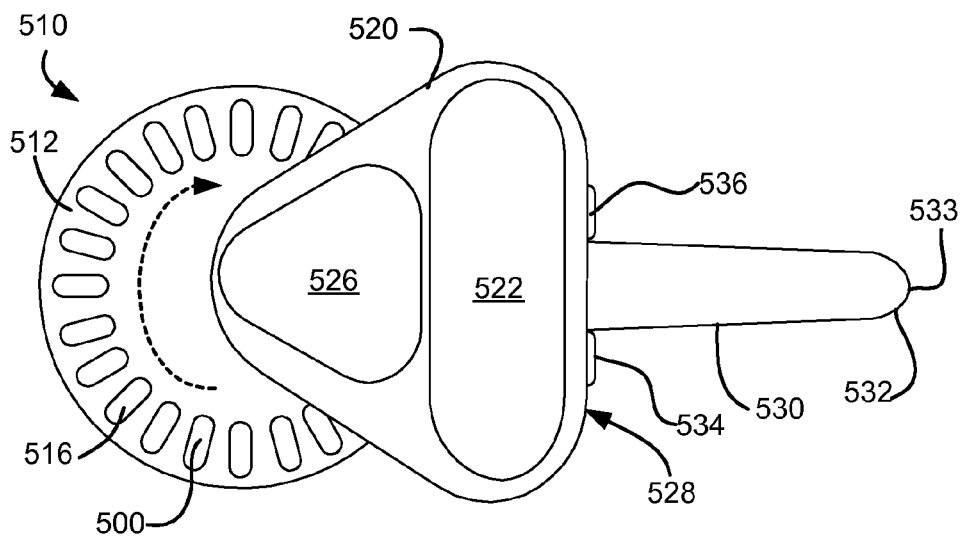
FIG. 5A shows a top view of an alternative drug delivery device according to an embodiment of the present invention.
Figure 5B:
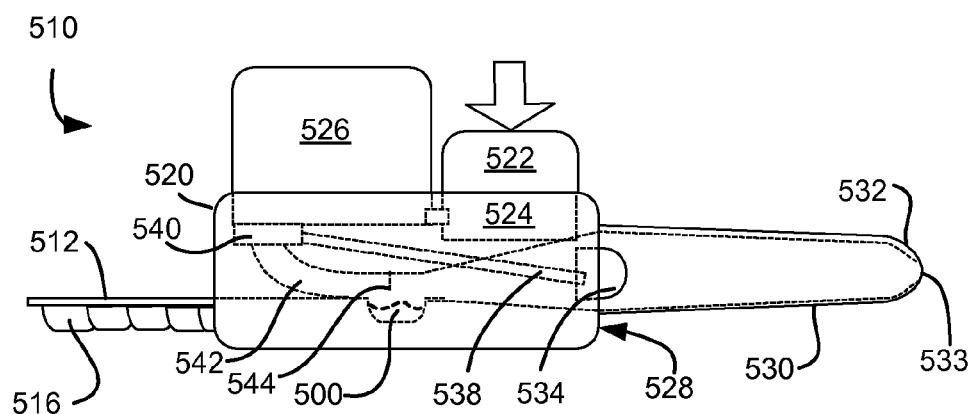
FIG. 5B shows a side view of the drug delivery device of FIG. 5A.

FIGS. 5A and 5B show an alternative drug delivery device 510 to supply a therapeutic agent in/through a pneumostoma. FIG. 5A is a top down view of drug delivery device 510 and FIG. 5B is a side view of the same device. The drug delivery device 510 is a dry powder drug delivery device. The therapeutic agent 500 in finely ground microcrystalline form is stored in a circular blister pack 512. One dose of therapeutic agent 500 is located in each blister 516. In some cases the blister pack 512 may be removed and replaced in other cases, drug delivery device 510 is discarded after all the doses in one blister pack have been used.

As shown in FIGS. 5A and 5B drug delivery device 510 includes a body 520 which receives blister pack 512. Blister pack 512 is supported such that it can rotate in body 520 and index one blister 516 at a time to a dispensing position within body 520. Body 520 also carriers a manual actuator 522 on the upper surface which operates a pumping mechanism 524 to force air into reservoir 526. Pumping mechanism 524 is pressure limited so that the maximum pressure of air in reservoir 526 is capped at a safe limit. Reservoir 526 (and/or tube 542) may also be provided with a safety valve to release any excess pressure. Body 520 has a front surface 528 for making contact with the skin of the patient surrounding the pneumostoma and limiting insertion of tube 530 to a safe depth. The size of tube 540 is selected so as to fit in the pneumostoma without causing injury. Tube 530 has an atraumatic tip 532 at its distal end and an opening 533 through which the therapeutic agent is delivered into the pneumostoma. Two trigger buttons 534, 536 protrude from front surface 528 of body 520. The trigger buttons are connected by a linkage 538 to a valve 540 of reservoir 524.

To operate drug delivery device 510 the patient depresses the manual actuator 522 one or more times. A pressure sensitive indicator (for example venting of a relief valve) indicates when sufficient pressure has been achieved. Tube 530 is then pushed into the pneumostoma. When tube 530 is introduced into the pneumostoma, the trigger buttons 534 and 536 contact the skin of the patient surrounding the pneumostoma. When slight pressure is applied to both trigger buttons 534, 536, linkage 538 opens valve 540 and the air in reservoir 524 escapes via tube 542 over a blister 516 containing the therapeutic agent. One or more baffles 544 is provided to provide turbulence to ensure that all of the microcrystalline therapeutic agent is picked up and distributed in the stream of air and pushed through tube 530 and out of opening 533 into the pneumostoma. In alternative embodiments, a manually operable trigger may be provided instead of trigger button 534 or 536.

Drug delivery device 510 is illustrative of an alternative therapeutic agent dispenser system which does not require a cylinder of compressed gas or propellant but instead depends on pumping action by the patient. Additionally, trigger buttons 534 and 536 fire drug delivery device 510 automatically when the correct position in the pneumostoma is reached. Drug delivery device 510 has an integrated tube and insertion stop. However, in alternative embodiments, the dry powder therapeutic agent dispensing mechanism of FIGS. 5A, 5B may be incorporated in the other drug delivery devices discussed herein.

Figure 6:
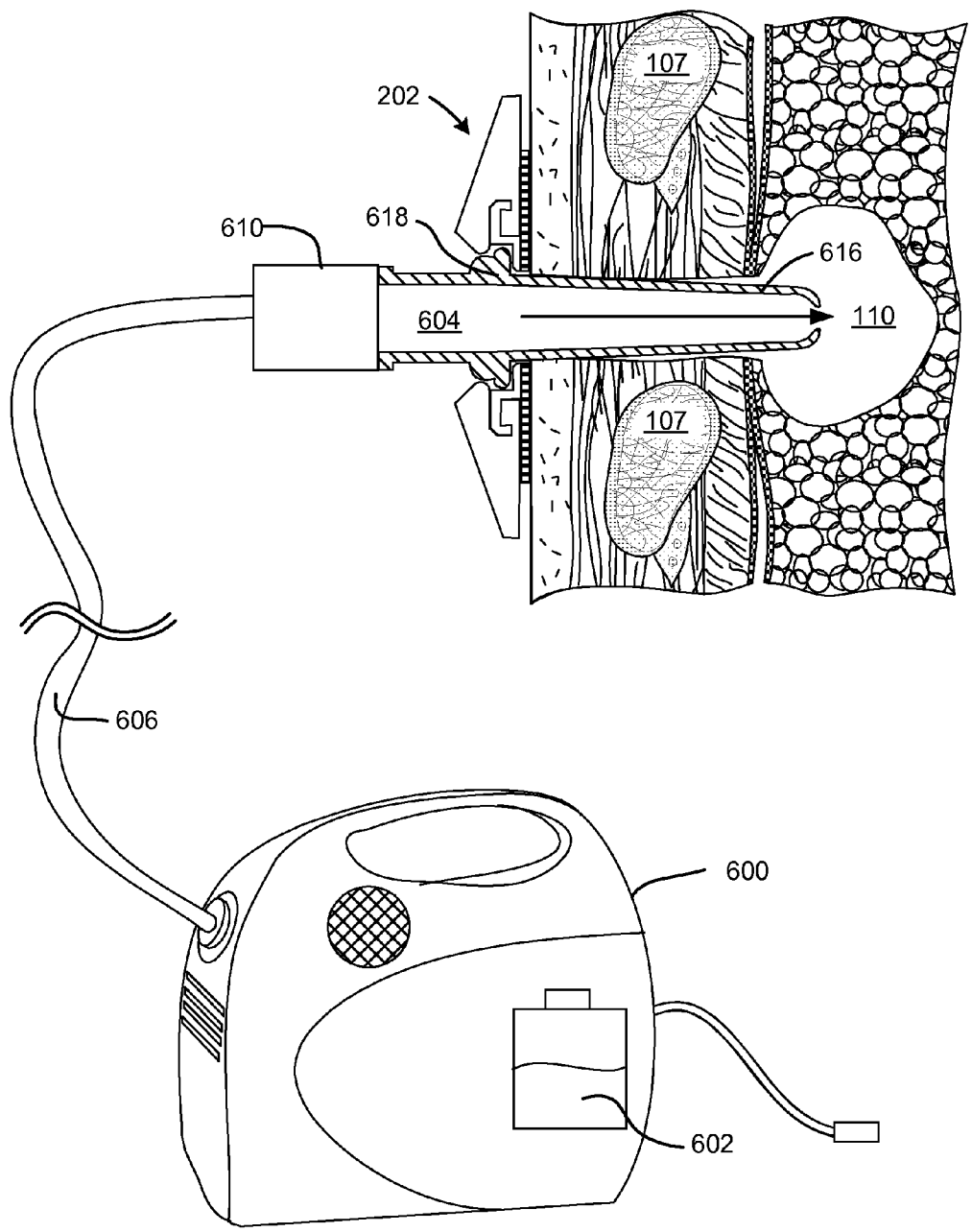
FIG. 6 shows a drug delivery device for use in conjunction with a nebulizer.

FIG. 6 shows an example of a drug delivery device 610 in the form of an adapter for coupling a nebulizer 600 to a chest mount 202 in order to introduce a therapeutic agent 602 into a pneumostoma 110. Nebulizer 600 is a device used to administer medication to people in the form of a vapor/mist. Nebulizer 600 pumps air or oxygen through a liquid therapeutic agent 602 (which may be liquid compound or a solution or suspension of a therapeutic agent in a carrier liquid) to turn it into a vapor/mist 604, which is then introduced to the patient via pneumostoma 110. Alternatively the nebulizer produces the vapor/mist ultrasonically or using a vibrating micromesh. As shown in FIG. 6, nebulizer 600 provides a vapor/mist 604 of therapeutic agent 602 under a regulated low positive pressure through conduit 606 to drug delivery device 610. Drug delivery device 610 includes a tube 616 which enters pneumostoma 610. At the proximal end of tube 616 is a coupling 618 which engages chest mount 202 to releasably secure drug delivery device 610 to chest mount 202 and within pneumostoma 110 while preventing over-insertion of tube 616. In alternative embodiments drug delivery device 610 may be integrated with a flange which engages the chest of the patient surrounding the pneumostoma directly to releasably secure the drug delivery device to the chest the patient and prevent over insertion of tube 616.

Nebulizers such as nebulizer 600 of FIG. 6 are typically plug-in devices that the patient may use for home treatment. In use, the patient would typically remove the pneumostoma vent from the chest mount 202 and insert the drug delivery device 610 connected to nebulizer 600. Typically a specific amount of a therapeutic agent is mixed with a specific volume of sterile water or saline and loaded into the nebulizer. The patient would then operate the nebulizer to provide the dose of therapeutic agent for a desired period of time or until the entire dose is delivered. The patient continues to breathe normally during this process. As the patient breathes, the therapeutic agent will be supplied via pneumostoma 110 into the parenchymal tissue of the lung. The therapeutic agent will then be dispersed efficiently throughout the lung by the process of collateral ventilation. Collateral ventilation is the term given to leakage of air through the connective tissue between the alveoli. Collateral ventilation may include leakage of air through pathways that include the interalveolar pores of Kohn, bronchiole-alveolar communications of Lambert, and interbronchiolar pathways of Martin.

Drug delivery using a nebulizer may have benefits over a single pulse delivery of drugs. Using a nebulizer allows for multiple breaths which may allow the therapeutic agent to effectively reach further into the parenchymal tissue allowing for better distribution and absorption. Incorporating a one-way valve or constant positive pressure through the delivery conduit of the conduit may also be used to ensure that the drug is moving into the lung. However, it is unnecessary for the nebulizer to provide gas at positive pressure to introduce the aerosol, mist or powder into the lung through the pneumostoma. The nebulizer may provide an aerosol, mist or powder suspended in air/gas at or near ambient pressure. Reduced pressure in the pneumostoma during inhalation by the patient creates a sufficient pressure differential to suck the aerosol, mist or powder suspended in air/gas into the pneumostoma. A one way valve is configured to prevent air (and therapeutic agent) from being exhaled out of the pneumostoma when the patient exhales. Alternatively, the nebulizer may provide a slight positive pressure using a fan, pump or the like.

The use of nebulizer 600, as shown in FIG. 6, avoids common disadvantages of inhaled nebulizers. When using inhaled nebulized therapeutic agents, the patient must wear a mask thus making communication difficult. Also, the inhaled agents often taste unpleasant and may cause undesirable side effects in tissues outside the lung, such as the mouth. Drug delivery device 610 of FIG. 6 delivers the therapeutic agent directly to the lung tissue via pneumostoma 110 thereby increasing efficiency of the delivery and reducing discomfort to the patient. The drug delivery device 610 may also be advantageously utilized to deliver low pressure therapeutic gases to the patient, for example, oxygen.

Figure 7A:
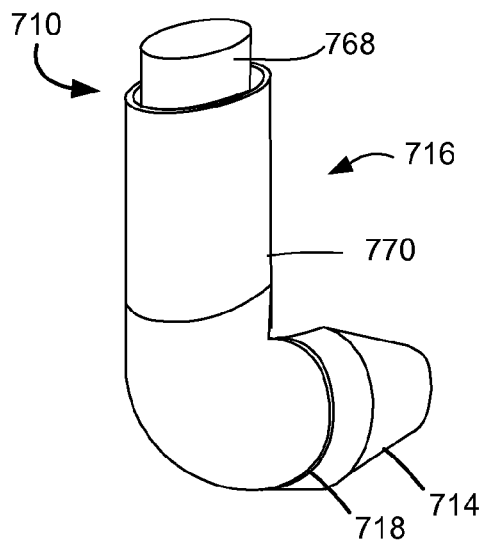
FIGS. 7A and 7B show views of an alternative drug delivery device according to an embodiment of the present invention.
Figure 7B:
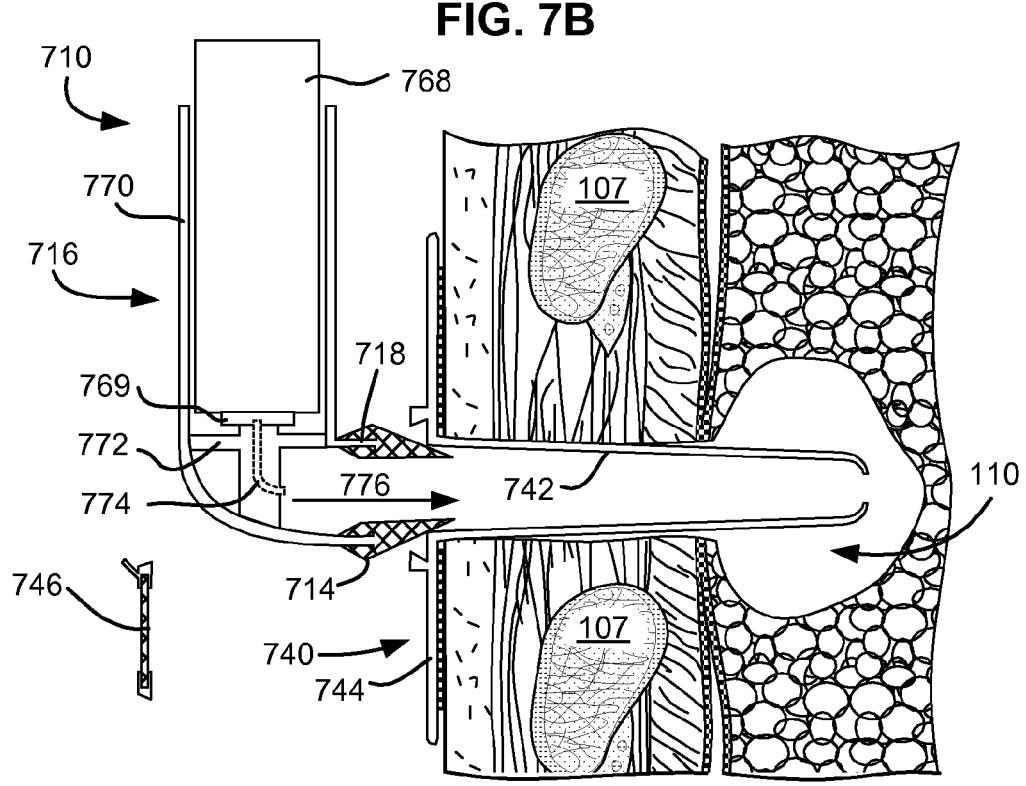

FIGS. 7A and 7B show views of an alternative drug delivery device 710 according to an embodiment of the present invention. FIG. 7A shows a perspective view of an alternative drug delivery device 710. FIG. 7B shows a sectional view of the drug delivery device 710. As shown in FIG. 7A, drug delivery device 710 includes a therapeutic agent dispenser 716 attached to a conical flange 714. Conical flange 714 is formed of a compliant material such that it can form a seal when pushed against a PMD. The conical shape is designed to center drug delivery device 710 over a PMD to facilitate engagement of the PMD by the drug delivery device 710. Conical flange 714 may be provided with surface features to enhance the formation of a temporary seal between flange 714 and the PMD. A joint 718 is shown between therapeutic agent dispenser 716 and conical flange 714 because it is preferred that a stiffer material be used for therapeutic agent dispenser 716 and a more flexible material be used for conical flange 714 which mates with the PMD. The parts may be formed separately and then joined by welding, gluing or otherwise bonding/connecting. Note that, for safety reasons, each of the components of drug delivery device 710 is preferably too large to fit through the tube 742 of a PMD. This prevents aspiration of any of the components into the lung even in the event of damage to drug delivery device 710.

As shown in FIG. 7B, drug delivery device 710 includes a pressurized canister 768 is received in a sleeve 770. The outlet valve 769 of pressurized canister 768 engages a fixture 772 in the bottom of sleeve 770. When the user pushes canister 768 down into sleeve 770, fixture 772 activates valve 769 to release a metered dose of therapeutic agent in a propellant gas. The therapeutic agent and gas passes through a channel 774 in fixture 772 and are ejected into and through tube conical flange 714 as shown by arrow 776. The alternative drug delivery mechanisms previously discussed may also be used with a drug delivery device having a PMD interface shown in FIG. 7B.

As shown in FIG. 7B, the drug delivery device 710 operates in conjunction with a pneumostoma management device (PMD) 740 located within a pneumostoma 110. In the PMD 740 of FIG. 7B, tube 742 is formed in one piece with (or permanently attached to) a flange 744. PMD 740 has a hydrophobic filter 746 press fit into the proximal end of tube 742 which may be removed to allow use of drug delivery device 710 (as shown in FIG. 7B). Drug delivery device 710 may however be used or modified to be used with a PMD having a different design than shown in FIG. 7B.

As shown in FIG. 7B, conical flange 714 provides a mating section designed to mate and make a temporary seal with PMD 740. As shown in FIG. 7B, to use drug delivery device 710, hydrophobic filter 746 is first removed from PMD 740. Conical flange 714 is then pushed into contact with the opening of tube 742. The tip of conical flange 714 fits in the space left by the removal of hydrophobic filter 746. Conical flange 714 centers drug delivery device 710 as it is pushed into tube 742. Conical flange 714 also deforms slightly to make a seal against PMD 740. When conical flange 714 has formed a temporary seal with PMD 740, therapeutic agent dispenser 716 is operated to dispense the therapeutic agent through the tube 742 of PMD 740 into the pneumostoma 110. The patient holds drug delivery device 710 against PMD 740 during dispensing the therapeutic agent and for some seconds thereafter (preferably 3-30 seconds). After dispensing the therapeutic agent, the drug delivery device 710 is removed and the hydrophobic filter 746 is press fit into the proximal end of the tube 742. Alternatively PMD 740 may be replaced with a new PMD 740.

Figure 8A:
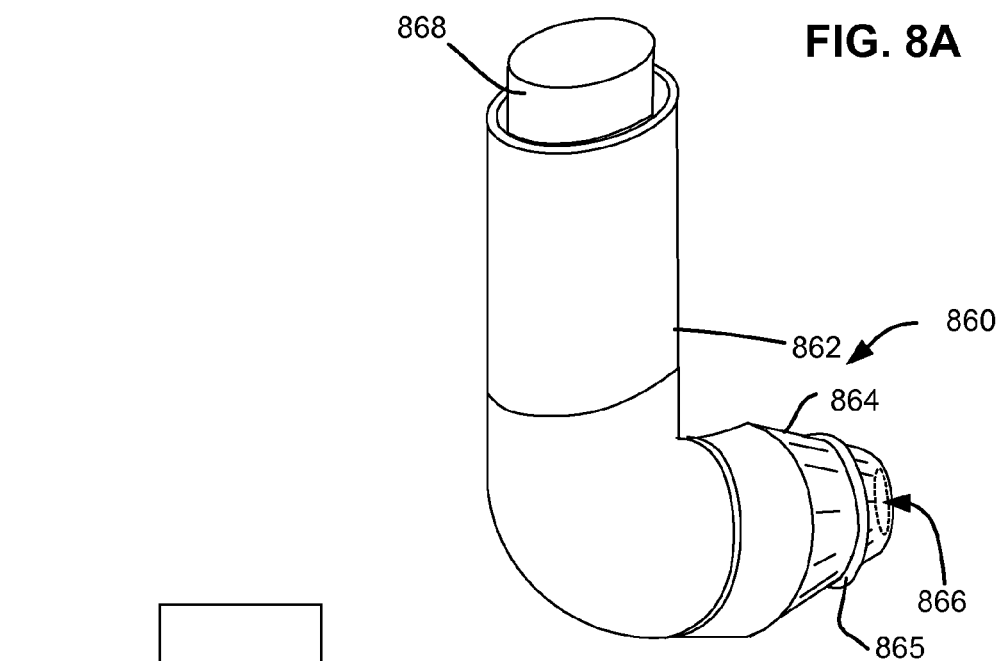
FIG. 8A shows a perspective view of a drug delivery device designed to operate with the pneumostoma management device of FIGS. 2A and 2B according to an alternate embodiment of the present invention.
Figure 8B:
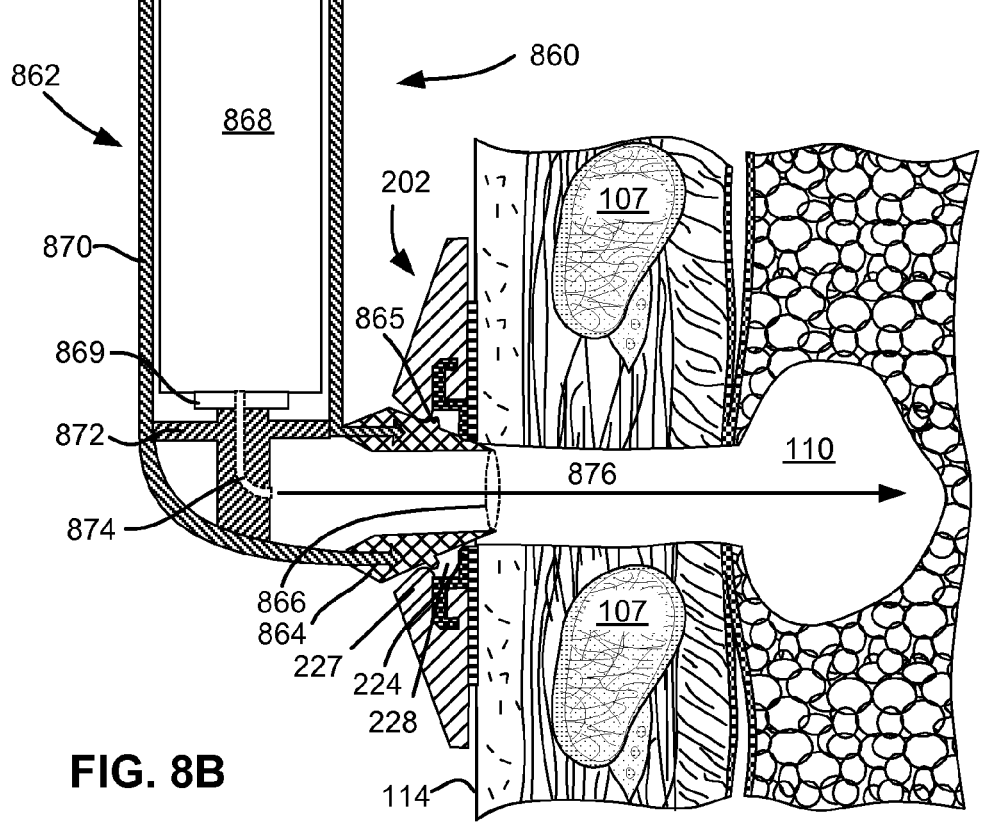
FIG. 8B shows a sectional view of the drug delivery device of FIG. 8A mated with the pneumostoma management device of FIGS. 2A and 2B.

Referring now to FIGS. 8A and 8B which show views of an alternate drug delivery device 860 designed to be used in conjunction with PMD 801 of FIGS. 8A and 8B as part of a pneumostoma management system. FIG. 8A shows a perspective view of drug delivery device 860. FIG. 8B shows a sectional view through drug delivery device 860 of FIG. 8A when engaged with a chest mount 802. As shown in FIGS. 8A and 8B, drug delivery device 860 includes a therapeutic agent dispenser 862 and a coupling 864. Drug delivery device 860 is configured such that coupling 864 may be easily engaged with aperture 224 of a chest mount 202. Coupling 864 is designed such that it is too large to pass through aperture 224 of chest mount 202 thereby preventing insertion of drug delivery device 260 into pneumostoma 110. Coupling 864 may optionally be provided with a feature such as a lip 865 for releasably engaging lip 227 of recess 228 of chest mount 202.

As shown in FIGS. 8A and 8B, coupling 864 is cone-shaped being somewhat narrower at the distal end for ease of insertion into the chest mount 202. The coupling has an aperture 866 in the distal end (shown by dashed line). The conical coupling facilitates the engagement of the chest mount 202 by the drug delivery device 860. It is advantageous to simplify this engagement in order to allow the patients to more readily comply with their drug delivery protocols. The conical coupling also self centers over the pneumostoma 110. Even if the coupling 864 is off center when it first contacts chest mount 202, the conical shape pushes coupling 864 towards center as it enter chest mount 202.

It is also preferable for coupling 860 to make a good seal with the chest mount 202 so that leakage of propellant gas and therapeutic agents is reduced and delivery to the pneumostoma is increased. For this reason, the coupling 864 is preferably made of a relatively soft and compliant material that makes a good seal with chest mount 202 when pushed up against chest mount 202 with a modicum of force. The outer surface of coupling 864 may also be provided with structural features to promote such sealing e.g. ridge 865. In combination, the features of coupling 864 serve to increase delivery of the therapeutic agent to the pneumostoma.

Therapeutic agent dispenser 862 includes a mechanism for providing an aerosol, mist or powder in suspended in a propellant gas under sufficient positive pressure to enter the lung through the tube. The therapeutic agent dispenser preferably provides positive pressure to push the therapeutic agent into the pneumostoma. Suitable therapeutic agent dispenser mechanisms for providing metered doses of therapeutic agents in a propellant gas are known. Suitable therapeutic agent dispensers include therapeutic agent dispensing mechanisms found in nebulizers, ultrasonic nebulizers, metered dose inhalers and dry powder inhalers. Dry powder therapeutic agent dispensers deliver a fine microcrystalline suspension of therapeutic agent.

Referring again to FIGS. 8A and 8B therapeutic agent dispenser 862 includes a pressurized canister 868 received in a sleeve 870. The outlet valve 869 of canister 868 engages a fixture 872 in the bottom of sleeve 870. When the user pushes canister 868 down into sleeve 870, fixture 872 activates valve 869 to release a metered dose of therapeutic agent in a propellant gas. The therapeutic agent and propellant gas pass through a channel 874 in fixture 870 and are ejected into through aperture 866 of coupling 864, through aperture 224 of chest mount 202 and into pneumostoma 110 as shown by arrow 876.

Note that in some embodiments it is unnecessary for therapeutic agent dispenser 862 to provide a propellant gas at positive pressure to introduce the aerosol, mist or powder into the lung through the pneumostoma. In some embodiments the therapeutic agent dispenser 862 provides the therapeutic agent/gas mixture at or near ambient pressure. Reduced pressure in the pneumostoma during inhalation by the patient creates a pressure differential which sucks the therapeutic agent suspended in air/gas into the pneumostoma.

Chest mount 202 is first positioned over a pneumostoma and secured with adhesive to the skin of the patient. In a preferred embodiment, the chest mount 202 remains attached for up to a week thereby avoiding irritation of the skin caused by daily attachment and removal of a mount. Chest mount may be positioned by the patient by manual alignment of the aperture 224 of chest mount 202 with the aperture of the pneumostoma 112. Alternatively a pneumostoma vent or an alignment tool may be used to align the chest mount.

To use drug delivery device 860 in combination with chest mount 202 Drug delivery device 860 is then inserted through the aperture in the chest mount until coupling 864 engages the chest mount 202. Drug delivery device 860 is pushed up against chest mount 202 so that coupling 864 centers aperture 866 over aperture 224 of the chest mount and pneumostoma 112. Pushing drug delivery device 860 against chest mount 202 also serve to make a temporary seal between coupling 864 and chest mount 202. The temporary seal reduces leakage of therapeutic agent. Drug delivery device 860 is then operated to supply the aerosolized or dry powder therapeutic agent directly to the parenchymal tissue of the lung through pneumostoma 112 by operation of therapeutic agent dispenser 862. The drug delivery device 860 may be operated either by the patient, caregiver or medical practitioner.

FIG. 8C shows an example of a method of using a drug delivery device according to embodiments of the present invention. The method may be described in instructions for use provided to the patient with the drug delivery device. At step 880, the patient adjusts the pneumostoma management device. Depending on the operation of the drug delivery device, this step may involve, for example, removing a component of the pneumostoma vent such as the filter; or removing the pneumostoma vent. At step 882, the patient loads a dose of the therapeutic agent into the drug delivery device. In some cases, the therapeutic agent is provided in single dose containers and thus this will involve loading a single dose package or indexing a package containing multiple singe dose containers to a full container. In other cases, the therapeutic agent will be in a multiple-use container, such as a pressurized metered dose canister and it will be unnecessary for the patient to load a therapeutic agent dose unless the container is empty. The drug delivery device is now prepared for operation.

At step 884, the patient positions the distal end of the coupling in the aperture of the chest mount or pneumostoma vent and pushes the drug delivery device against the chest mount or pneumostoma vent (which serves to accurately position aperture 866 of the drug delivery device and make a temporary seal between coupling 864 and chest mount 202). As the distal end of the coupling enters the aperture it centers the coupling. As the distal tip is pushed against the aperture, the compliant surface makes a temporary seal against the pneumostoma vent and/or chest mount. After the coupling has centered and self-sealed, the therapeutic agent may be administered.

In a typical therapeutic agent delivery operation the patient will first exhale through the nose/mouth at step 885 immediately prior to actuating the drug delivery device. At step 886 the drug delivery device is actuated to mix the therapeutic agents (aerosol, gas or dry powder) in the propellant/air. In some embodiments this mixing step requires a relatively high air speed/pressure. It may be undesirable for this airspeed/pressure to be applied to the pneumostoma and thus the location of mixing step 886 may be separated by features to reduce the airspeed/pressure distance before the mixture reaches the pneumostoma. Such features may include, for example, space, volume, baffles and the like. At step 888 application of positive pressure is used to propel the mixture of therapeutic agent and propellant into the pneumostoma and/or through the pneumostoma into the lung. The positive pressure applied at this step may be substantially less than the pressure used at step 886. The positive pressure may be supplied by a different mechanism or by a modulation of the same mechanism. Steps 886 and 888 may be combined in one step for example where the pressure is modulated by the mechanics of the device such that a higher local pressure is available in one part of the device to mix the agent but is reduced by the time it reaches the pneumostoma. Note that in some embodiments it is unnecessary for the therapeutic agent dispenser to provide propellant gas at positive pressure to introduce the aerosol, mist or powder into the lung through the pneumostoma. In some embodiments the drug delivery device remains at or near ambient pressure and reduced pressure in the pneumostoma during inhalation by the patient creates a pressure differential which sucks the aerosol, mist or powder suspended in air/gas into the pneumostoma.

At step 890, air is introduced through the pneumostoma to aid distribution of the therapeutic agent through the lung tissue by collateral ventilation. Step 890 is optional and may in some cases be combined with step 888. In some cases step 890 may be achieved by the patient "inhaling" through the pneumostoma in which the patient expands the ribcage thereby creating a negative pressure in the chest to draw air in through the pneumostoma. In some circumstances this "inhalation" through the pneumostoma may be enhanced by obstructing the nose and mouth while expanding the ribcage. However, step 890 may not be necessary and a therapeutic agent may be efficiently distributed from the pneumostoma through parenchymal tissue of the lung by collateral ventilation without the need for additional intake of air through the pneumostoma.

At step 892, the patient optionally holds their breath for a time prior to exhaling, such as 10 to 15 seconds. This step may not be necessary for therapeutic agents delivered into the pneumostoma. Because the therapeutic agent was not delivered through the natural airways, it will not be rapidly exhaled through the natural airways. Indeed, in some cases breathing normally (while obstructing the pneumostoma) while cause rapid distribution of the therapeutic agent through the lung with little loss of therapeutic agent due to exhalation. In some case it may be advantageous to provide a slight positive pressure of air to the pneumostoma after delivery of the therapeutic agent to promote diffusion of the therapeutic agent through the lung. Steps 884 and 892 may be repeated a number of times if necessary to deliver multiple doses of therapeutic agent as shown by dashed arrow 894.

It may be desirable to leave the drug delivery device in place for a period after delivery of therapeutic agent to prevent the agent from being ejected through the pneumostoma. After the therapeutic agent has been delivered, the drug delivery device is pulled away from the chest mount and/or pneumostoma vent at step 896. At step 898, any removed components of the pneumostoma management device are reattached. Any or all of the above steps may be performed and/or controlled by a physician or caregiver instead of the patient. The therapeutic agent delivery steps may be repeated according to a particular dosing schedule or as needed depending on the therapeutic agent and/or physician's instructions.

Figure 9A:
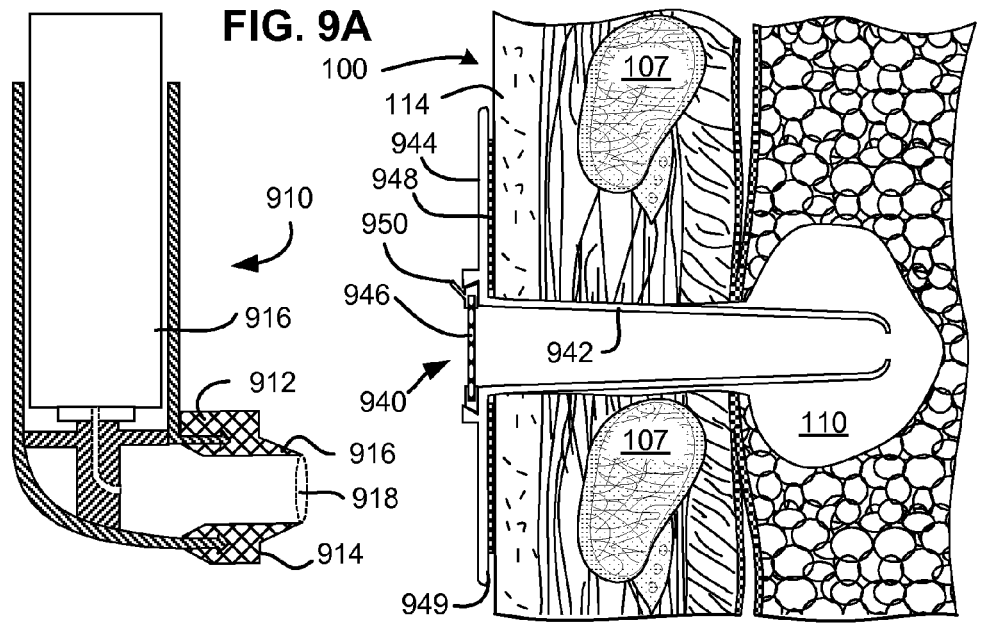
FIGS. 9A and 9B show sectional views of an alternative drug delivery device according to an embodiment of the present invention.
Figure 9B:
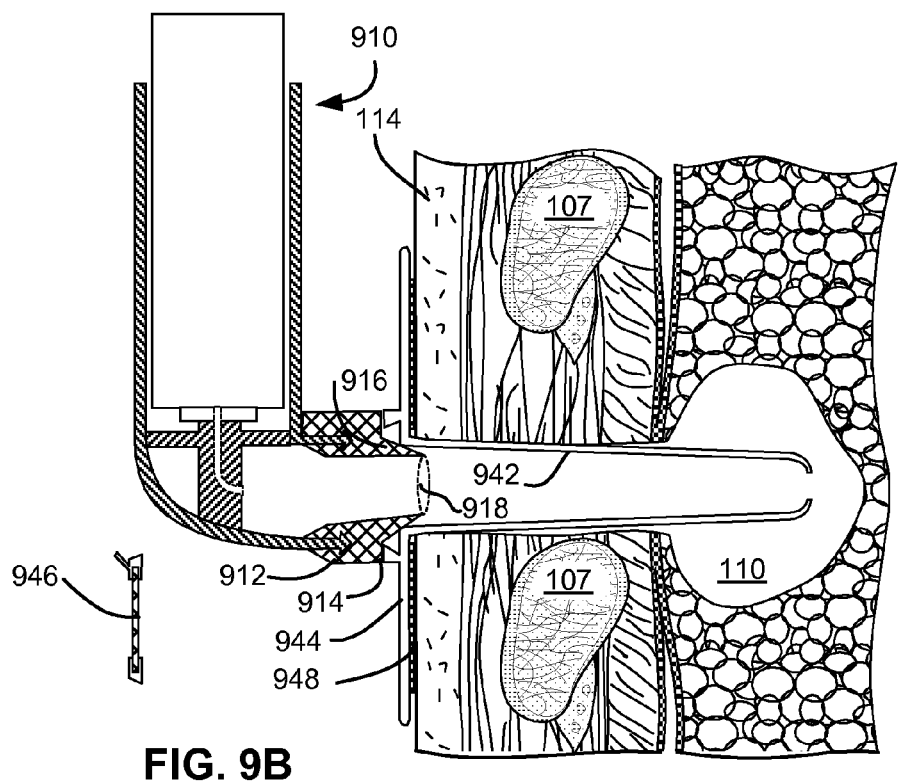

FIGS. 9A and 9B show an alternative drug delivery device 910 to supply a therapeutic agent in/through a pneumostoma. The drug delivery device 910 operates in conjunction with a pneumostoma management device (PMD) 940 located within a pneumostoma 110. In the PMD 940 of FIGS. 9A and 9B, tube 942 is formed in one piece with (or permanently attached to) a flange 944. PMD 940 has a hydrophobic filter 946 press fit into the proximal end of tube 942 and has a biocompatible adhesive 948 on the contact surface 949 of flange 944 for releasably securing flange 944 to the skin 114 of the patient's chest 100. As shown in FIG. 9D, drug delivery device 910 has a mating section 912, having a mating surface 914 designed to mate and make a temporary seal with the exterior surface of flange 944. Mating section 912 also has a distal tip 916 designed to aid in the coupling of mating section 912 with PMD 940.

Drug delivery device 940 is utilized with PMD 940 while the tube 942 of PMD 940 is within pneumostoma 110. As shown in FIG. 9A, to use drug delivery device 910, hydrophobic filter 946 is first removed by pulling on tab 950. Distal tip 916 of mating section 912 is placed against PMD 940. Distal tip 916 guides mating section 912 into the aperture of PMD 940. As drug delivery device 910 is pushed towards PMD 940, distal tip 916 centers mating section 912 over the aperture in the PMD 940 aligning aperture 918 with the PMD 940. Mating surface 914 of mating section 912 contacts flange 944. Mating section 914 is made of a compliant material and thus forms a temporary seal between the drug deliver device 910 and the PMD 940. In this embodiment, mating section 912 fits in the space left by the removal of hydrophobic filter 946 as shown in FIG. 9B. When mating section 912 has formed a temporary seal with flange 944, therapeutic agent dispenser 916 is operated to dispense the therapeutic agent through the tube 942 of PMD 940 into the pneumostoma 110. After dispensing the therapeutic agent, the drug delivery device 910 is removed and the hydrophobic filter 946 is press fit into the proximal end of the tube 942. Alternatively PMD 940 may be replaced with a new PMD 940.

Pneumostoma Assessment Using Gas

Measurement of gases entering or leaving the pneumostoma may be useful for assessing the functionality of the pneumostoma. The ability of gas to pass through the pneumostoma may be measured in a number of ways. First, gas flow through the pneumostoma can be measured passively by placing a device over the pneumostoma which measures airflow out of and/or into the pneumostoma during regular breathing of the patient. Essentially, gases exiting the pneumostoma are collected by a system which records the volume of gas. Additionally, the gas may be analyzed to determine composition of the gases exiting the pneumostoma.

As shown in FIG. 10A, a gas analysis device 1000 is inserted into the pneumostoma 110 of a patient. Gas analysis device 1000 is connected by tube 1002 to gas analyzer 1012. The gases exhaled from the pneumostoma 110 may then be examined during normal breathing or during an exercise test. The exhaled gas may be examined to determine oxygen and carbon dioxide concentrations. In some cases, the concentrations are compared to oxygen and carbon dioxide concentrations in the gases exhaled through the natural airways. Such evaluation may be useful in determining the effectiveness of a pneumostoma and the location and/or desirability of additional pneumostomas. The output of gas analyzer 1012 may be provided to a computer system 1014 to display the results of the gas analysis. Optionally, a mask 1016 may be provided. Mask 1016 may be used to measure the volume of gas inhaled and exhaled by the patient through the natural airways. The volume of gas inhaled and exhaled through the natural airways may be compared to the volume of gas exiting the pneumostoma.

In another example, a diagnostic gas is introduced through the natural airways and the expiration of gases from the pneumostoma is measured. As shown in FIG. 10A, optional mask 1016 may be used to provide a diagnostic gas mixture 1018 via the natural airways. The concentration of gases exiting the pneumostoma 110 may be compared to the concentration of gases in the diagnostic gas supply 1018. The time-course of exhalation of diagnostic gases through the pneumostoma may be analyzed by gas analyzer 1012 to evaluate the function of the pneumostoma and the prevalence of collateral ventilation pathways connecting the pneumostoma to the remainder of the lung. Such evaluation may be useful in determining the effectiveness of a pneumostoma and the location and/or desirability of additional pneumostomas. Gas analysis equipment may be connected to a PMD and/or pneumostoma using one of the several techniques and mechanisms described herein.

Alternatively, gas may be provided through the pneumostoma from outside the chest of the patient. The gas is preferably supplied at a controlled pressure slightly above the ambient air pressure so as not to cause injury to the pneumostoma. In a simple case, the rate of flow of gas into the lung through the pneumostoma may be measured. The rate of gas flow may be used to assess the patency of the pneumostoma. Alternatively, diagnostic gases may be introduced through the pneumostoma for assessing collateral ventilation and gas exchange. Diagnostic gases may be helpful in measuring functional attributes of the pneumostoma and the lung. In particular, introduction of diagnostic gases through the pneumostoma may be useful for assessing gas diffusion between the pneumostoma and the lung.

In one example, a diagnostic gas is introduced through the pneumostoma and the gas is measured as it is exhaled through the natural airways. The diagnostic gas may, for example, be a gas mixture such as DLCO gas used in diffusion spirometry (which nominally consists of 10% helium, 3000 ppm carbon monoxide and the balance air). Gases exhaled through the natural airways are analyzed to determine gas concentrations. The time course of exhalation of the diagnostic gas is indicative of factors such as pneumostoma functionality and collateral ventilation. Where the diagnostic gas is introduced via the pneumostoma the time course of exhalation of gas through the natural airways may be analyzed to evaluate the function of the pneumostoma and the prevalence of collateral ventilation pathways connecting the pneumostoma to the remainder of the lung. Such evaluation may be useful in determining the effectiveness of a pneumostoma and the location and/or desirability of additional pneumostomas. A supply of the diagnostic gas may be connected to a PMD and/or pneumostoma using one of the several techniques and mechanisms described herein.

FIG. 10B shows a schematic view of a lung assessment system using introduction of diagnostic gas 1018 through a pneumostoma 110. As shown in FIG. 10B a gas analysis device 1000 is inserted into the pneumostoma 110 of a patient. Gas analysis device 1000 is connected by tube 1002 to a pressure regulated source of diagnostic gas 1018. A solenoid-controlled valve 1006 in tube 1002 controls the flow of diagnostic gas into pneumostoma 110. The patient is provided with a mask 1016 which allows the patient to inhale ambient air but that collects the exhaled air and passes it to gas analyzer 1012. During exhalation, a portion of the exhaled gases is collected in a sample collection system and then analyzed using discrete gas sensors and/or a gas chromatograph. The gas analyzer 1012 and the solenoid-controlled valve 1006 are connected to a control system 1020 which may be a general purpose computer. Control system 1020 controls solenoid-controlled valve 1006 and receives data from gas analyzer 1012. Control system 1020 analyzes the gas concentrations in the gas exhaled by the patient and factors the relative values with inspired gas volume and other parameters to calculate factors related to collateral ventilation and pneumostoma function.

Introduction of diagnostic gases through a pneumostoma may also be used to enhance imaging the lung with a CT scan or NMR scan. For example polarized Helium-3 may be utilized to enhance nuclear magnetic resonance/magnetic resonance imaging of the lung (analogous to the way contrast agents enhance X-ray imaging). For example, polarized helium-3 may be produced with lasers and the magnetized pressurized gas may be stored for several days. When introduced into the lung, the polarized helium-3 can be imaged with an MRI-like scanner which produces breath-by-breath images of lung ventilation, in real-time. Polarized helium-3 may thus, be used to visualize airways in static or dynamic fashion. Alternative gases which may be used as visualization agents include gaseous radionuclide xenon or technetium DTPA in an aerosol form.

Introducing a controlled amount of a visualizable gas, e.g. polarized Helium-3, through the pneumostoma and imaging the diffusion of the gas into the lung over time may be utilized for quantitative evaluation of the function of the pneumostoma and the prevalence of collateral ventilation pathways connecting the pneumostoma to the parenchymal tissue of the lung. Measuring the time-course variations in diffusion of Helium-3 into the lung allows analysis of diffusion coefficients for areas of the lung. Such evaluation may be useful in determining the effectiveness of a pneumostoma and the location and/or desirability of additional pneumostomas. A source of polarized Helium-3 may be connected to a PMD and/or pneumostoma using one of the several techniques and mechanisms described herein.

FIG. 10C shows a schematic view of a lung assessment system using a diagnostic gas in conjunction with an imaging scanner 1050. Scanner 1050 may be an MRI, NMR, CT or X-Ray so long as the particular diagnostic gas used may be successfully imaged with the system. As shown in FIG. 10B, gas analysis device 1000 is inserted into the pneumostoma 110 of a patient. Gas analysis device 1000 is connected by tube 1030 to a pressure-regulated source of a visualizable gas (e.g. polarized Helium-3). A solenoid-controlled valve 1032 in tube 1030 controls the flow of diagnostic gas into pneumostoma 110. The scanner 1050 and the solenoid-controlled valve 1032 are connected to a control system 1020 (not shown) which may be a general purpose computer. The control system 1020 (not shown) controls solenoid-controlled valve 1032 and receives data from scanner 1050. The control system 1020 coordinates the introduction of diagnostic gas into the patient with the patient's breathing and also with the operations of scanner 1050 in order to accurately image dispersion of the diagnostic gas from the pneumostoma 110 to other parts of the lung. Control system 1020 analyzes the time course distribution of the diagnostic gas from the pneumostoma into the lung tissues to calculate factors related to collateral ventilation and pneumostoma function, e.g. diffusion coefficients.

FIGS. 10D and 10E show views of the gas analysis device 1000 of FIGS. 10A-10C. FIG. 10D shows a perspective view of the gas analysis device 1000 while FIG. 10E shows a sectional view of gas analysis device 1000 positioned within a pneumostoma. In general terms, gas analysis device 1000 is a device which can be secured into a pneumostoma for sampling gases exiting the pneumostoma and/or providing gases into the pneumostoma. Gas analysis device 1000 can form part of a system which utilizes such gas sampling or gas provision for assessment of pneumostoma function and/or lung function. As used in FIGS. 10A and 10C, gas analysis device 1000 is used to introduce diagnostic gas into the pneumostoma. As used in FIG. 10B, gas analysis device 1000 is used to collect gases exhaled from the lung for analysis by gas analyzer 1012.

Referring to FIG. 10D, gas analysis device 1000 includes a hollow tube 1060 for insertion into the pneumostoma. Hollow tube 1060 is surrounded by a flange 1062 which secures tube 1060 in position in the pneumostoma. Hollow tube 1060 connects to a coupling 1064 on the proximal side of flange 1062. Coupling 1064 is configured so that tube 1002 may be readily connected and disconnected. Hollow tube 1060 has one or more holes 1066 at the distal end through which gas may pass into or out of the pneumostoma. Hollow tube 1060 and flange 1062 also provide a temporary seal which inhibits leakage of gas from around hollow tube 1060.

FIG. 10E shows a sectional view of gas analysis device 1000 of FIGS. 10A-4D in position in a pneumostoma 110. It is preferable to minimize leakage of gases into or out of the pneumostoma. Flange 1062 is thus provided with an adhesive coating 1068 on the distal surface to provide a temporary seal between the gas analysis device 1000 and the skin of the chest of the patient. Surface features may also be provided on the distal surface of flange 1062 or on tube 1060 to promote sealing between gas analysis device 1000 and the pneumostoma. For example, a circular ridge 1070 is shown in section on FIG. 10E. Gas analysis device 1000 is preferably a disposable component that will be used only with one patient. One or more filters may be interposed between gas analysis device 1000 and the gas supply and/or gas analyzer to prevent possible cross-contamination between patients.

Delivery of Therapeutic Agents by the PMD/Vent

The tube of a PMD such as pneumostoma vent system 1100 may be designed to deliver a pharmaceutically-active substance. A "pharmaceutically-active substance" is an active ingredient of vegetable, animal or synthetic origin which is used in a suitable dosage as a therapeutic agent for influencing conditions or functions of the body, as a replacement for active ingredients naturally produced by the human or animal body and to eliminate or neutralize disease pathogens or exogenous substances. The release of the substance in the environment of pneumostoma vent has an effect on the course of healing and/or counteracts pathological changes in the tissue due to the presence of pneumostoma vent. In particular, it is desirable in some embodiments to coat or impregnate pneumostoma vent with pharmaceutically-active substances that preserve the patency of pneumostoma and/or are antimicrobial in nature but that do not unduly irritate the tissues of the pneumostoma. In particular cases, suitable pharmaceutically-active substances may have an anti-inflammatory and/or antiproliferative and/or spasmolytic and/or endothelium-forming effect, so that the functionality of the pneumostoma is maintained. However the pneumostoma vent may also deliver, be coated with or be impregnated with time-release therapeutic agents design to have effects on tissues other than the tissues of the pneumostoma. Suitable pharmaceutically-active substances include those described above.

FIGS. 11A-11C shows different views of a pneumostoma vent system 1100 (a pneumostoma management device). Pneumostoma vent system 1100 is designed for use without a chest mount although it could be adapted for use with a chest mount. FIG. 11A shows an exploded view of the four main components of pneumostoma vent system. From right to left these components are annular adhesive cover 1102, filter 1104, pneumostoma vent 1106 and hydrocolloid ring 1108.

Annular adhesive cover 1102 is a thin porous biocompatible membrane which is adhesive on the surface facing the pneumostoma (the inner surface see 1122 in FIG. 11C) and non-adhesive on the outer surface 1120. A suitable material for annular adhesive cover 1102 is a CHG Chlorhexidine Gluconate IV Securement Dressing available under the Tradename TEGADERM™ from 3M of St. Paul, Minn. TEGADERM™ is thin layer of polyurethane bonded to a thin hydrocolloid adhesive layer. The film is biocompatible as well as thin, strong, and breathable. Other thin biocompatible dressings and adhesive films may be used as an alternative to TEGADERM™ Annular cover 1102 has an aperture 1124 large enough to allow air to exit through filter 1104. Aperture 1124 may however be slightly smaller than filter 1104 so that annular cover can be used to secure filter 1104 to pneumostoma vent 1106. Exposed portions of annular adhesive cover 1102 are provided with a paper cover to protect the adhesive ring prior to use.

Filter 1104 is a circular disc of filter material. Filter 1104 is preferably a hydrophobic filter material, for example GORE-TEX. Filter 1104 is larger than the proximal aperture in pneumostoma vent 1106 and is positioned over the proximal aperture to filter material moving in and out of the pneumostoma vent 1106. Filter 1104 may be secured to pneumostoma vent 1106 by and adhesive, welding, or other bonding technology. Filter 1104 may also be secured to pneumostoma vent 1106 by annular adhesive cover 1102 instead of or in addition to other bonding techniques.

Pneumostoma vent 1106 comprises a tube 1130 for entering the pneumostoma. As previously discussed, tube 1130 has an atraumatic tip 1165 and one or more apertures 1167 in the distal end to allows gases and discharge to enter tube 1130 from the pneumostoma. Tube 1130 is connected to a flange 1132 at the proximal end. Flange 1132 may be formed in one piece with tube 1130 or formed separately and joined to tube 1132 as previously described with respect to other embodiments. The proximal opening 1163 of pneumostoma vent is sized so that filter 1104 covers proximal opening 1163. Filter 1104 is secured over proximal opening 1163 as described in the previous paragraph.

Hydrocolloid ring 1108 is a biocompatible hydrocolloid material which is adhesive on both sides. Hydrocolloid ring may be provided with a film coating and a transitional adhesive on the side facing flange 1132 and annular cover 1102 in order to better secure hydrocolloid ring 1108 to the flange and annular cover. Hydrocolloid ring 1108 is preferably less than 3 mm thick and is more preferably, approximately 1 mm in thickness. Exposed portions of hydrocolloid ring 1108 are provided with a paper cover to protect the adhesive ring prior to use.

Pneumostoma vent system 1100 may be provided as a kit of separate components or one or more of the components may be preassembled when provided to the patient. FIG. 11B shows an assembly of all four main components including annular adhesive cover 1102, filter 1104, pneumostoma vent 1106 and hydrocolloid ring 1108. Note that tube 1130 fits through the middle of hydrocolloid ring 1108. Note also that flange 1132 is trapped between annular adhesive cover 1102 and hydrocolloid ring 1108. In this embodiment, filter 1104 is also secured to pneumostoma vent 1106 by annular adhesive cover 1102. Exposed adhesive regions of annular adhesive ring 1102 and hydrocolloid ring 1108 on the patient side of the pneumostoma vent system assembly are provided with protective covers (for example paper covers) to protect the adhesive during shipping and prior to use. The completed or partially completed assembly is provided as a sterile product to the patient or caregiver who inserts the pneumostoma vent into a pneumostoma as part of a pneumostoma care program.

FIG. 11C shows a sectional view of the pneumostoma vent system 1100 in position within a pneumostoma 110. As shown in FIG. 11C, tube 1130 is inserted into the pneumostoma and passes through the chest wall into the lung. Aperture 1167 in the distal end of tube 1130 is positioned inside the lung so that gases and discharge may enter the tube 1130 of the pneumostoma vent system. Flange 1132 of pneumostoma vent 1106 is secured to the skin of the patient by hydrocolloid ring 1108 and annular adhesive cover 1102. Flange 1132 secures the position of tube 1130 within pneumostoma 110. Flange 1132 secures the position of aperture 1163 on the chest of the patient such that gases from the lung may vent through tube 1130 and filter 1104. Both hydrocolloid ring 1108 and annular adhesive cover 1102 contact the skin 114 of the patient to secure the pneumostoma vent system. In some cases a barrier film may be applied by the patient prior to securing the pneumostoma vent system to reduce skin irritation caused by application and removal of the system. An additional ring of absorbent material (not shown), for example, gauze or another absorbent fabric may be positioned around tube 1130 between hydrocolloid ring 1108 and the skin 114 of the patient for absorbing any discharge from pneumostoma 110 which escapes around tube 1130.

The components of the pneumostoma management system are preferably supplied to the patient in sterile packaging. In preferred embodiments, the components are supplied in packaging that assists the patient in utilizing the components of the system in the correct sequence. The packaging should include instructions for use. The packaging may also be printed with material that assists the patient in the appropriate sequence of the steps for using the enclosed components. The package may also be designed to provide the components to the patient in the order required for use and maintain sterility during use. For example, the package may be designed so that, upon opening the package, the components are physically laid out in a tray in the order in which they are to be used by the patient. Alternatively, the components may be provided as individual components separately packaged. For example, cleaning and moisturizing swabs and barrier spray/cream may alternatively or additionally be packaged separately and provided to patient.

Referring again to FIG. 11C which shows a sectional view of the pneumostoma vent system 1100 in position within a pneumostoma 110. As shown in FIG. 11C, tube 1130 is inserted into the pneumostoma and passes through the chest wall into the lung. Tube 1130 may be coated with a pharmaceutically-active substance along all or part of tube 1130.

As shown in FIG. 11C tube 1130 is provided with a pharmaceutically-active coating 1140 including a pharmaceutically-active substance. Coating 1140 is limited to the distal tip of tube 1140. However coating may also be provided over the entirety of tube 1130 or different coatings provided in different regions of tube 1140 depending upon the intended function of the coating. Coating 1140 is in contact with thin vascularized epithelium of the pneumostoma at the perimeter of pneumostoma 110. Thus depending on the pharmaceutical, the pharmaceutically-active substance may diffuse from coating 1140 into the cells of the pneumostoma, and from those cells into the bloodstream of the patient. The coating 1140 preferably releases the pharmaceutically-active substance over the time of use (such as a day) to main dosage consistency. The pharmaceutically-active substance may be selected to treat the tissues of the pneumostoma for example to maintain patency, reduce tissue growth, or inhibit infection. The pharmaceutically active substance may alternatively be selected to treat the patient systemically for example by providing a hormone to be absorbed into the blood stream via the tissues of the pneumostoma.

As shown in FIG. 11C the material of tube 1130 of pneumostoma vent system 1100 may also be impregnated with a pharmaceutically-active substance 1142. Depending upon the material, the pharmaceutically-active substance may be added before or after forming the material into the desired shape. The pharmaceutically-active substance is eluted from the tube 1130 over time while the tube 1130 is in contact with the pneumostoma. The tube 1130 preferably releases the pharmaceutically-active substance gradually over the time of use (such as a day) to main dosage consistency. The pharmaceutically-active substance may be selected to treat the tissues of the pneumostoma for example to maintain patency, reduce tissue growth, or inhibit infection. The pharmaceutically-active substance may alternatively be selected to treat the patient systemically for example by providing a hormone to absorbed into the blood stream via the tissues of the pneumostoma.

Figure 11D:
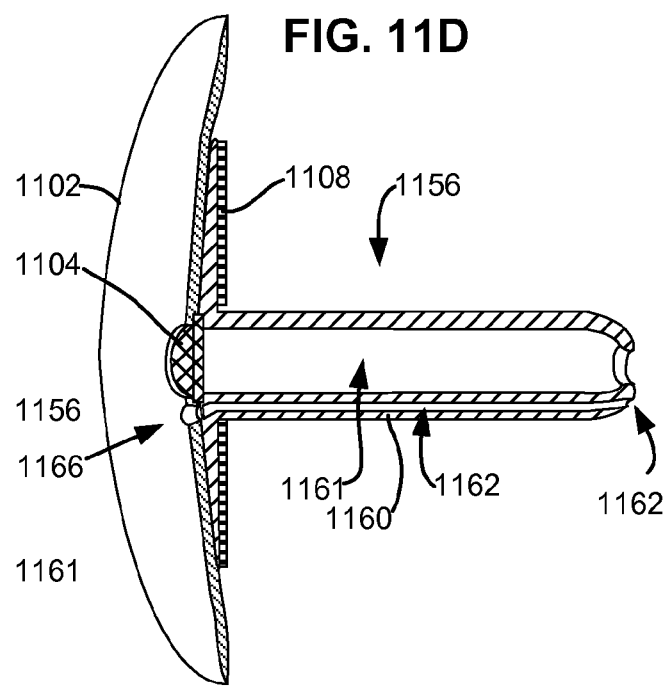
FIGS. 11D and 11E show vies of a pneumostoma management device having drug infusion features.

FIG. 11D shows an alternate embodiment of a pneumostoma vent system 1150 with drug delivery features. As before, pneumostoma vent system includes filter 1104, annular adhesive cover 1102, hydrocolloid ring 1108. However vent 1156 comprises a tube 1160 for entering the pneumostoma which has an additional lumen 1162 for delivery of a pharmaceutically active substance fluid in addition to the lumen 1161 through gases may escape from the pneumostoma. Lumen 1161 passes along the length of tube 1130 and exits tube 1130 at one or more apertures 1164. One or more apertures 1164 are preferably located in the distal half of tube 1160 so as to releases the pharmaceutically active fluid into contact with highly vascularized tissue in the lung to facilitate absorption. Vent 1156 has a flange 1158 at the proximal end. Lumen 1162 is accessible through flange 1158 by means of access port 1166. Access port 1166 marks the location of lumen 1162. Access port 1166 is preferably closed until mated with a device for supplying the pharmaceutically active fluid into lumen 1162.

Figure 11E:
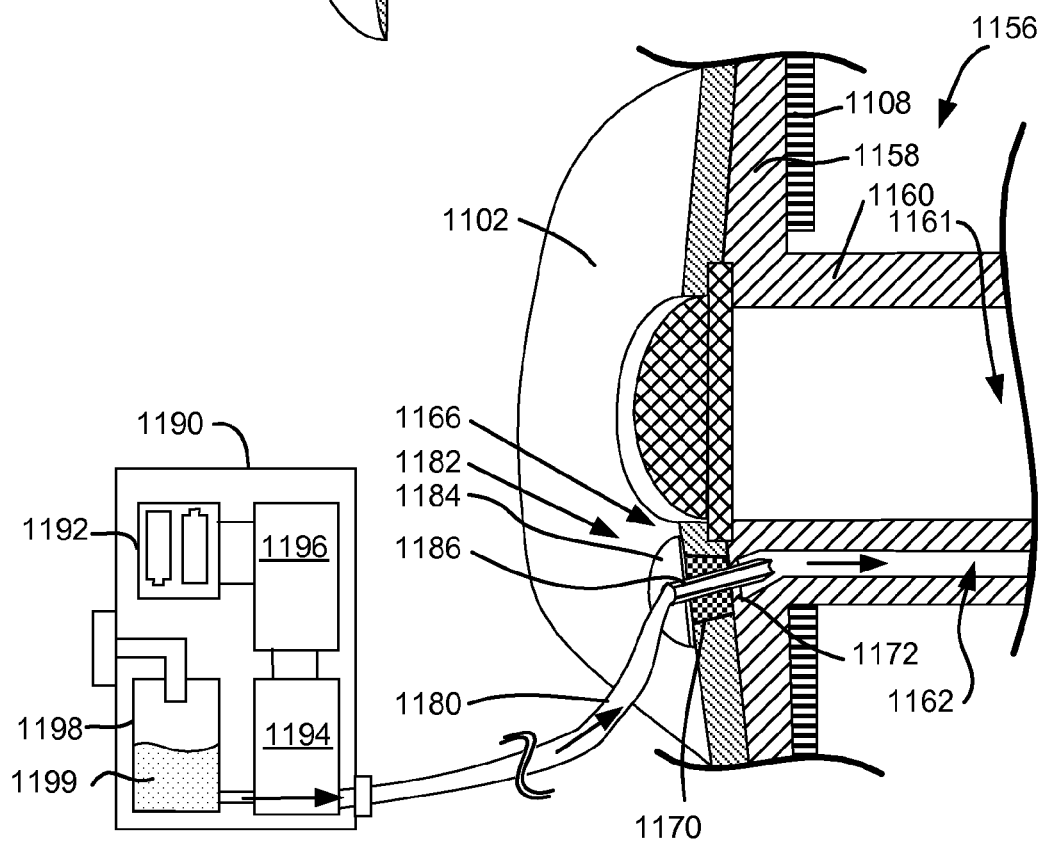

FIG. 11E shows an enlarged view of an embodiment of an access port 1166. As shown in FIG. 11E access port 1166 is marked by an opening 1170 in adhesive cover 1102 which exposes flange 1158. The distal end of lumen 1162 is obstructed by a diaphragm 1172. Diaphragm 1172 may be formed from cover 1102, the material of flange 1158 or an additional thin piece of material. To access lumen 1162 the sharp tip of a tube (not shown) pierces the diaphragm allowing a fluid to be injected through the tube into the lumen 1162. For example a syringe may be used with a short needle to inject a pharmaceutically-active fluid through diaphragm into lumen 1162. The fluid passes along lumen 1162 and out of aperture 1162 9 FIG. 11D) into the pneumostoma where it may be absorbed. This is a suitable technique for periodic or intermittent supply of a pharmaceutically-active fluid to the patient. Where a continuous, regular and/or automatic supply of pharmaceutically-active fluid is desired, a supply line 1180 may be coupled to lumen 1162 as shown in FIG. 11E. Supply line 1180 is connected by a coupling 1182 to access port 1166. Coupling 1182 may include an adhesive flange 1184 and a short needle 1186. Short hollow needle 1186 penetrates diaphragm 1172 to connect supply line 1180 to lumen 1162. Access port 1166 and coupling 1182 may include other suitable medical connectors for connecting one tube to another, for example, Luer or Tuohy Borst fittings. The other end (proximal end) of supply line 1180 is connected to a drug pump 1190. Drug pump 1190 (shown schematically) is preferably a self-contained ambulatory unit having a power supply 1192, pump 1194, pump controller 1196 and a reservoir 1198 containing a supply of the pharmaceutically-active fluid 1199. Drug pump 1190 may be, for example a belt mounted unit approximately the size of a cell phone. Pump 1194 pumps a metered supply of the pharmaceutically-active fluid 1199 from the reservoir 1198 into the supply line 1180 under the control of controller 1196 and powered by power supply 1192. Suitable portable drug pumps are known in the art and described, for example, in U.S. Pat. No. 7,347,836 to Peterson et al. and references cited therein.

In use, controller 1196 meters the amount of pharmaceutically-active fluid 1199 supplied to the patient according to preset programming, user input or sensors. For example, where the pharmaceutically-active fluid is insulin or an insulin analog, controller 1196 may cause pump 1194 to supply insulin to supply line 1180 in response to elevated glucose levels detected by a glucose sensor. From supply line 1180 the pharmaceutically-active fluid 1199 passes through coupling 1182 and access port 1166 via lumen 1162 into the pneumostoma where it is absorbed into the bloodstream of the patient. The present invention has the advantage of providing a means for continuous administration and rapid absorption of the pharmaceutically-active fluid 1199 without requiring injection through the skin or oral administration.

Materials

In preferred embodiments, the PMD and drug delivery device are formed from biocompatible polymers or biocompatible metals. A patient will typically wear PMD at all times and thus the materials, particularly of tubes entering the pneumostoma, should meet high standards for biocompatibility. In general preferred materials for manufacturing the PMD and drug delivery device are biocompatible thermoplastic elastomers that are readily utilized in injection molding and extrusion processing. As will be appreciated, other suitable similarly biocompatible thermoplastic or thermoplastic polymer materials can be used without departing from the scope of the invention. Biocompatible polymers for manufacturing PMD and drug delivery device may be selected from the group consisting of polyethylenes (HDPE), polyvinyl chloride, polyacrylates (polyethyl acrylate and polymethyl acrylate, polymethyl methacrylate, polymethyl-coethyl acrylate, ethylene/ethyl acrylate), polycarbonate urethane (BIONATEG), polysiloxanes (silicones), polytetrafluoroethylene (PTFE, GORE-TEX®, ethylene/chlorotrifluoroethylene copolymer, aliphatic polyesters, ethylene/tetrafluoroethylene copolymer), polyketones (polyaryletheretherketone, polyetheretherketone, polyetherether-ketoneketone, polyetherketoneetherketoneketone polyetherketone), polyether block amides (PEBAX, PEBA), polyamides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, polyphosphazenes, nylon, polypropylene, polybutester, nylon and polyester, polymer foams (from carbonates, styrene, for example) as well as the copolymers and blends of the classes listed and/or the class of thermoplastics and elastomers in general. Reference to appropriate polymers that can be used for manufacturing PMD and drug delivery device can be found in the following documents: PCT Publication WO 02/02158, entitled "Bio-Compatible Polymeric Materials;" PCT Publication WO 02/00275, entitled "Bio-Compatible Polymeric Materials;" and, PCT Publication WO 02/00270, entitled "Bio-Compatible Polymeric Materials" all of which are incorporated herein by reference. Other suitable materials for the manufacture of the PMD include medical grade inorganic materials such stainless steel, titanium, ceramics and coated materials. Hydrophobic filter materials should be sufficiently porous to allow air to exit through the filter. Materials for hydrophobic filters are available commercially and filters can be fabricated from any suitable hydrophobic polymer, such as tetrafluoroethylene, PTFE, polyolefins, microglass, polyethylene and polypropylene or a mixture thereof. In preferred examples, the hydrophobic filter is a laminated tetrafluoroethylene e.g. TEFLON®, (E.I. du Pont de Nemours Co.) or GORE-TEX® (W.L. Gore, Inc.) of a controlled pore size. In other examples the hydrophobic filter may comprise a felted polypropylene; PTFE/polypropylene filter media.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. Embodiments of the present invention may use some or all of the features shown in the various disclosed embodiments where such features are not structurally or functionally incompatible. It is intended that the scope of the invention be defined by the claims and their equivalents.

What is claimed is:

1. A medical agent delivery system for delivering a medical agent through an artificial channel which passes through a chest wall, parietal membrane, visceral membrane and into a lung of a patient there being a seal between the visceral membrane and parietal membrane surrounding the artificial channel, the medical agent delivery system comprising:
a first device which includes, a tube adapted to be placed through the artificial channel such that a distal end of the tube is positioned within the lung of the patient, a flange connected to a proximal end of the tube adapted to secure the first device to the chest wall of the patient and position the tube within the artificial channel, and an aperture at the proximal end of the tube; and
a second device including, a container adapted to contain at least one dose of the medical agent, a dispensing port that interfaces with the aperture of the first device, and an actuator to release the medical agent;
whereby, with the tube of first device positioned in the artificial channel and the dispensing port of the second device interfaced to the aperture of the first device, operation of the actuator releases the medical agent through the dispensing port via the aperture and tube of the first device through the chest wall and into the lung of the patient.

2. The system of claim 1, wherein the dispensing port of the second device includes a compliant flange that can seal against the aperture of the first device.

3. The system of claim 1 wherein said second device is a nebulizer, and the medical agent is a therapeutic agent.

4. The system of claim 1 wherein the second device is a gas analyzer and the medical agent is a diagnostic agent.

5. The system of claim 1 wherein the second device is adapted to release the medical agent which is one of a therapeutic agent and a diagnostic agent.

6. The system of claim 1 wherein the dispensing port of the second device is self-centering and self-sealing with the aperture of the first device.

7. The system of claim 1 wherein the dispensing port of the second device includes a conical flange that can engage the aperture of the first device.

8. The system of claim 1 wherein the first device includes a second tube with a distal end of the second tube adapted to be positioned in the lung and a proximal end of the second tube including a second aperture.

9. The system of claim 1 wherein the first device includes a second tube with a distal end of the second tube adapted to be positioned in the lung and a proximal end of the second tube including a second aperture with a filter included at said second aperture.

10. The system of claim 1 wherein said container of said second device is adapted to contain a plurality of individual dosages of the medical agent.

11. A diagnostic system for use in association with an artificial channel which passes through a chest wall, a parietal membrane, a visceral membrane and the parietal membrane surrounding the artificial channel, the diagnostic system comprising:
a first device which includes:
a tube adapted to be place in the artificial channel such that a distal end of the tube is positioned within the lung of the patient,
a flange connected to a proximal end of the tube adapted to secure the first device to the chest wall of the patient and with the tube with the artificial channel and an aperture at the proximal end of the tube;
a second device that can connect to the aperture of the first device;
said second device including a diagnostic device that can at least one of provide a diagnostic agent through the tube to the lung and receive a sample of gases through the tub from the lung.

12. The diagnostic system of claim 11 wherein the second device is a gas analyzer.

13. The diagnostic system of claim 11 wherein the second device is an imaging system.

14. The diagnostic system of claim 11 wherein said first device includes a second tube that is placed in the artificial channel such that a distal end of the second tube is positioned within the lung of the patient and a proximal end of the second tube includes a second aperture and wherein the second device can provide a diagnostic agent through one of the first and second tubes and said second device can receive a sample of gases through the other of the first and second tubes from the lung.

15. The diagnostic system of claim 11 wherein said first device includes a second tube that is placed in the artificial channel such that a distal end of the second tube is positioned within the lung of the patient and a proximal end of the second tube includes a second aperture and wherein at least one of the first aperture and the second aperture has a filter.

16. A medical agent delivery system for delivering a medical agent through an artificial channel which passes through chest wall, parietal membrane, visceral membrane and into a lung of a patient, there being a seal between the visceral membrane and the parietal membrane, the medical agent delivery system comprising:
- a pneumostoma management first device which includes a tube adapted to be placed in the artificial channel such that a distal end of the tube is positioned within the lung of a patient,
- a flange connected to a proximal end of the tube adapted to secure the pneumostoma management device to the chest wall of the patient and with the tube within the artificial channel, and an aperture at the proximal end of the tube; and
- a medical agent delivery second device includes a self-sealing dispensing port that can selectively communicate with the aperture of the pneumostoma management device in order to provide the medical agent to the lung.

17. The system of claim 16 wherein the dispensing port of the second device includes a compliant flange that can seal against the aperture of the first device.

18. The system of claim 16 wherein said second device is a nebulizer and the medical agent is a therapeutic agent.

19. The system of claim 16 wherein the second device is a gas analyzer and the medical agent is a diagnostic agent.

20. The system of claim 16 wherein the second device is adapted to release the medical agent which is one of a therapeutic agent and a diagnostic agent.

21. The system of claim 16 wherein the dispensing port of the second device is self-centering and self-sealing with the aperture of the first device.

22. The system of claim 16 wherein the dispensing port of the second device includes a conical flange that can engage the aperture of the first device.

23. The system of claim 16 wherein the first device includes a second tube with a distal end of the second tube adapted to be positioned in the lung and a proximal end of the second tube including a second aperture.

24. The system of claim 16 wherein the first device includes a second tube with a distal end of the second tube adapted to be positioned in the lung and a proximal end of the second tube including a second aperture with a filter included at said second aperture.

25. The system of claim 16 wherein said container of said second device is adapted to contain a plurality of individual dosages of the medical agent.

* * * * *